United States Patent
Altman et al.

(10) Patent No.: US 9,085,610 B2
(45) Date of Patent: Jul. 21, 2015

(54) H. PYLORI LIPOPOLYSACCHARIDE OUTER CORE EPITOPE

(75) Inventors: Eleonora Altman, Ottawa (CA); Blair A. Harrison, Ottawa (CA); Vandana Chandan, Ottawa (CA)

(73) Assignee: National Research Council of Canada, Ottawa, Ontario ( * ) Notice: Subject to any disclaimer, the term of this patent is extended or adjusted under 35 U.S.C. 154(b) by 18 days.

(21) Appl. No.: 13/321,881

(22) PCT Filed: Jul. 30, 2010

(86) PCT No.: PCT/CA2010/001173
§ 371 (c)(1),
(2), (4) Date: Mar. 2, 2012

(87) PCT Pub. No.: WO2011/011879
PCT Pub. Date: Feb. 3, 2011

(65) Prior Publication Data
US 2012/0164145 A1 Jun. 28, 2012

Related U.S. Application Data

(60) Provisional application No. 61/230,315, filed on Jul. 31, 2009.

(51) Int. Cl.
*A61K 39/02* (2006.01)
*A61K 47/48* (2006.01)
*A61K 39/00* (2006.01)
*C08B 5/00* (2006.01)
*C07K 16/12* (2006.01)
*C08B 37/00* (2006.01)
*C08L 5/00* (2006.01)

(52) U.S. Cl.
CPC .............. *C07K 16/121* (2013.01); *A61K 39/105* (2013.01); *A61K 47/4823* (2013.01); *A61K 47/4833* (2013.01); *A61K 47/48261* (2013.01); *A61K 47/48284* (2013.01); *C08B 37/006* (2013.01); *C08L 5/00* (2013.01); *A61K 2039/505* (2013.01); *A61K 2039/6037* (2013.01); *A61K 2039/6081* (2013.01)

(58) Field of Classification Search
None
See application file for complete search history.

(56) References Cited

U.S. PATENT DOCUMENTS 6,765,091 B1   7/2004   Bencomo et al.
2007/0065465 A1*   3/2007   Lees et al. ............... 424/244.1

FOREIGN PATENT DOCUMENTS

CA   2762366   2/2011
WO   01/16146   3/2001
WO   2011/011879   2/2011

OTHER PUBLICATIONS

Campbell AM. In: Monoclonal Antibody Technology. Elsevier Science Publishers, The Netherlands, Chapter 1, pp. 1-32, 1984.*
Shin-ichi Yokota et al: "*Helicobacter pylori* Lipopolysaccharides Upregulate Toll-Like Receptor 4 Expression and Proliferation of Gastric Epithelial Cells via the MEK1/2-ERK1/2 Mitogen-Activated Protein Kinase Pathway", American Society for Microbiology, vol. 78, No. 1, Jan. 2010, pp. 468-476.
International Search Report and Written Opinion of Nov. 19, 2010 for PCT/CA2010/001173.
Altman E, Chandan V, Larocque S, Aubry A, Logan SM, Vinogradov E, Li J. Effect of the HP0159 ORF mutation on the lipopolysaccharide structure and colonizing ability of *Helicobacter pylori*. FEMS Immunol Med Microbiol 2008; 53: 204-213.
Altman E, Fernández H, Chandan V, Harrison BA, Wilson Schuster M, Otth Rademacher L, Toledo C. Analysis of *Helicobacter pylori* isolates from Chile: occurrence of a selective type 1 Lewis b antigen expression in lipopolysaccharide. J Med Microbiol 2008; 57: 585-591.
Altman E, Harrison BA, Hirama T, Chandan V, to R, MacKenzie R. Characterization of murine monoclonal antibodies against *Helicobacter pylori* lipopolysaccharide specific for Lex and Ley blood group antigens. Biochem Cell Biol 2005; 83: 589-596.
Altman E, Smirnova N, Li J, Aubry A, Logan SM. Occurrence of a nontypable *Helicobacter pylori* strain lacking Lewis blood group O antigens and DD-heptoglycan: evidence for the role of the core alpha1,6-glucan in colonization. Glycobiology 2003; 13: 777-783.
Anderson PW, Pichichero ME, Insel RA, Betts R, Eby R, Smith DH. Vaccines consisting of periodate-cleaved oligosaccharides from the capsule of *Haemophilus influenzae* type b coupled to a protein carrier: structural and temporal requirements for priming in the human infant. J Immunol 1986; 137: 1181-1186.

(Continued)

*Primary Examiner* — S. Devi
(74) *Attorney, Agent, or Firm* — Michael R. Williams; Ade & Company Inc.

(57) ABSTRACT

*Helicobacter pylori*, one of the most common human pathogens, is associated with the development of human chronic gastritis, peptic ulcers and gastric cancer. The invention relates to a α1,6-glucan-containing *Helicobacter pylori* compound comprising the structure of Formula (I): wherein R is a α-DDHep-3-α-L-Fuc-3-β-GlcNAc trisaccharide substituted with an α1,6-glucan linked to an α1,3-DD-heptan, and wherein the last DD-Hep residue of α1,3-DD-heptan is capped with β-GlcNAc residue. Compositions comprising the compound, uses of the compound, and antibodies raised against the compound are also described.

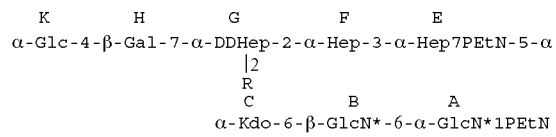

15 Claims, 9 Drawing Sheets

(56) References Cited

OTHER PUBLICATIONS

Angelakopoulos H, Hohmann EL. Pilot study of phoP/phoQ-deleted *Salmonella enterica* serovar Typhimurium expressing *Helicobacter pylori* urease in adult volunteers. Infect Immun 2000; 68: 2135-2141.

Appelmelk BJ, Simmons-Smit L, Negrini R, Moran AP, Aspinall GO, Forte JG et al. Potential role of molecular mimicry between *Helicobacter pylori* lipopolysaccharide and host Lewis blood group antigens in autoimmunity. Infect Immun 1996; 64: 2031-2040.

Brisson J-R, Crawford E, Uhrin D, Khieu NH, Perry MB, Severn WB, Richards JC. The core oligosaccharide component from Mannheimia (*Pasteurella*) haemolytica serotype A1 lipopolysaccharide contains L-glycero-D-manno- and D-glycero-D-manno-heptoses: Analysis of the structure and conformation by high-resolution NMR spectroscopy. Can J Chem 2002; 80: 949-963.

Castillo-Rojas G, Mazari-Hiriart M & López-Vidal Y (2004). *Helicobacter pylori:* focus on CagA and VacA major virulence factors. Salud pública de México 46: 538-548.

Chandan V, Logan SM, Harrison BA, Vinogradov E, Aubry A, Stupak J, Li J, Altman, E. Characterization of a waaF mutant of *Helicobacter pylori* strains 26695 provides evidence that an extended lipopolysaccharide structure has a limited role in the invasion of gastric cancer cells. Biochem Cell Biol 2007; 85: 582-590.

Chu C, Liu B, Watson D, Szu S, Bryla D, Shiloach J, Schneerson R, Robbins JB. Preparation, characterization, and immunogenicity of conjugates composed of the O-specific polysaccharide of *Shigella dysenteriae* type 1 (Shiga's *Bacillus*) bound to tetanus toxoid. Infect Immun 1991; 59: 4450-4458.

Ciucanu I, Kerek F. A simple and rapid method for the permethylation of carbohydrates. Carbohydr Res 2004; 131: 209-217.

Cox AD, Zou W, Gidney MAJ, Lacelle S, Plested JS, Makepeace K, Wright JC, Coull PA, Moxon ER, Richards JC. Candidacy of LPS-based glycoconjugates to prevent invasive meningococcal disease: Developmental chemistry and investigation of immunological responses following immunization of mice and rabbits. Vaccine 2005; 23: 5045-5054.

Dubois M, Gilles KA, Hamilton JK, Rebers PA, Smith, F. Colorimetric method for determination of sugars and related substances. Anal Chem 1956; 28: 350-356.

Dunn BE, Cohen H, Blaser MJ. *Helicobacter pylori*. Clin Microbiol Rev 1997; 10: 720-741.

Ellman GL. Tissue sulfhydryl groups. Arch Biochem Biophys 1959; 82: 70-77.

Fernández-Santana V, González-Lio R, Sarracent-Pérez J, Verez-Bencomo V. Conjugation of 5-azido-3-oxapentyl glycosides with thiolated proteins through the use of thiophilic derivatives. Glycoconjugate J 1998; 15: 549-553.

Gu X-X, Tsai C-M, Ueyama T, Barenkamp SJ, Robbins JB, Lim DJ. Synthesis, characterization, and immunological properties of detoxified lipooligosaccharide from nontypable *Haemophilus influenzae* conjugated to proteins. Infect Immun 1996; 64: 4047-4053.

Hiratsuka K, Logan SM, Conlan JW, Chandan V, Aubry A, Smirnova N, Ulrichsen H, Chan KHN, Griffith DW, Harrison BA, Li J, Altman E. Identification of a D-glycero-D-manno-heptosyltransferase gene from *Helicobacter pylori*. J Bacteriol 2005; 187: 5156-5165.

Holst O, Brade L, Kosma P, Brade, H. Structure, serological specificity, and synthesis of artificial glycoconjugates representing the genus-specific lipopolysaccharide epitope of *Chlamydia* spp. J Bacteriol 1991; 173:1862-1866.

Kohler G, Milstein C. Continuous cultures of fused cells secreting antibody of predefined specificity. Nature 1975; 256: 495-497.

Logan SM, Altman E, Mykytczuk O, Brisson J-R, Chandan V, St Michael F, Masson A, Leclerc S, Hiratsuka N, Smirnova N, Li J, Wu Y, Wakarchuk WW. Novel biosynthetic functions of lipopolysaccharide rfaJ homologs from *Helicobacter pylori*. Glycobiology 2005; 15: 721-733.

Logan SM, Conlan JW, Monteiro MA, Wakarchuk WW, Altman E. Functional genomics of *Helicobacter pylori:* identification of a b-1,4 galactosyltransferase and generation of mutants with altered lipopolysaccharide. Mol Microbiol 2000; 35: 1156-1167.

Mieszala M, Kogan G, Jennings HJ. Conjugation of meningococcal lipooligosaccharides through their lipid A terminus conserves their epitopes and results in conjugate vaccines having improved immunological properties. Carbohydr Res 2003; 338: 167-175.

Monteiro MA. *Helicobacter pylori:* a wolf in sheep's clothing: the glycotype families of *Helicobacter pylori* lipopolysaccharides expressing histo-blood groups: structure, biosynthesis, and role in pathogenesis. Adv Carbohydr Chem Biochem 2001; 57: 99-158.

Passwell JH, Harley E, Ashkenazi S, Chu C, Miron D, Ramon R, Farzan N, Shiloach J, Bryla DA, Majadly F, Roberson R, Robbins JB, Schneerson R. Safety and immunogenicity of improved *Shigella* O-specific polysaccharide-protein conjugate vaccines in adults in Israel. Infect Immun 2001; 69: 1351-1357.

Pon RA, Lussier M, Yang Q-L, Jennings HJ. N-Propionylated group B meningococcal polysaccharide mimics a unique bactericidal capsular epitope in group B *Neisseria meningitidis*. J Exp Med 1997; 185: 1929-1938.

Rossi G, Ruggiero P, Peppoloni S, Pancotto L, Fortuna D, Lauretti L, Volpini G, Mancianti S, Corazza M, Taccini E, Di Pisa F, Rappuoli R, Del Giudice G. Therapeutic vaccination against *Helicobacter pylori* in the beagle dog experimental model: safety, immunogenicity, and efficacy. Infect Immun 2004; 72: 3252-3259.

Roy, R., Katzenellenbogen, E., and Jennings, H.J. 1984. Improved procedures for the conjugation of oligosaccharides to protein by reductive amination. Can J. Biochem. Cell Biol. 62, 270-275.

Ruggiero P, Peppoloni S, Rappuoli R, Del Giudice G. The quest for a vaccine against *Helicobacter pylori:* how to move from mouse to man? Microbes Infect 2003; 5: 749-756.

Sawardeker JH, Sloneker JH, Jeannes A. Quantitative determination of monosaccharides as their alditol acetates by gas liquid chromatography. Anal Chem 1967; 39: 1602-1604.

Wirth HP, Yang M, Karita M, Blaser MJ. Expression of the human cell surface glycoconjugates Lewis X and Lewis Y by *Helicobacter pylori* isolates is related to cagA status. Infect Immun 1996; 64: 4598-4605.

Yokota, S., Amano, K., Fujii, N., Yokochi, T. Comparison of serum antibody titers to *Helicobacter pylori* lipopolysaccharides, CagA, VacA and partially purified cellular extracts in a Japanese population. FEMS Microbiol Lett 2000; 185: 193-198.

Yu S, Gu X-X. Biological and immunological characteristics of lipooligosaccharide-based conjugate vaccines for serotype C *Moraxella catarrhalis*. Infect Immun 2007; 75: 2974-2980.

Maina, n. H., Tenkanen, M., Maaheimo, H., Juvonen, R., Virkki, L.: NMR spectroscopic analysis of exopolysaccharides produced by *Leuconostoc citreum* and *Weissella con fusa*. Carbohydr. Res. 343, 1446-1455 (2008).

Harrison BA, Fernández H, Chandan V, Wilson Schuster M, Otth Rademacher L, Toledo C, Li J and Altman E. Characterization and functional activity of murine monoclonal antibodies specific for •1,6-glucanchain of *Helicobacter pylori* lipopolysaccharide. *Helicobacter* 2011; 16:459-67.

Altman, E., Chandan, V., Li, J., Vinogradov, E.: Lipopolysaccharide structures of *Helicobacter pylori* wild-type strain 26695 and 26695 HP0826::Kan mutant devoid of the O-chain polysaccharide component, Carbohydr. Res., 2011; 346: 2437-2444.

Altman E., Chandan V., Li J., Vinogradov E.: A re-investigation of the lipopolysaccharide tructure of *Helicobacter pylori* strain Sydney (SS1). FEBS J., 2011; 278: 3484-3493.

Reeves, Emer P., et al., *Helicobacter pylori* Lipopolysaccharide Interacts with TIFF1 in a pH-Dependent Manner, Gastroenterology 2008, 135, pp. 2043-2054.

Zhou, Wei-Ying, et al., Therapeutic efficacy of a multi-epitope vaccine against *Helicobacter pylori* infection in BALB/c mice model, Vaccine 27 (2009) 5013-5019.

Bromuro, Carla, et al., Beta-glucan-CRM197 conjugates as candidates antifungal vaccines, Vaccine 28 (2010) 2615-2623.

Sverremark, E., et al., Immunogenicity of bacterial carbohydrates: cholera toxin modulates the immune response against dextran B512, Immunology 1997 92 153-159.

Wood, Charles et al., Immunochemical Studies of Conjugates of Isomaltosyl Oligosaccharides to Lipid 1. Antigenicity of the

(56) References Cited

OTHER PUBLICATIONS

Glycolipids and the Production of Specific Antibodies in Rabbits, J. Exp. MED. vol. 154 Aug. 1981 432-449.

Verez-Bencomo, V., et al., A Synthetic Conjugate Polysaccharide Vaccine Against *Haemophilus influenzae* Type b, Jul. 23, 2004 vol. 305 Science www.sciencemag.org.

Fernández-Santana V, et al., Antigenicity and Immunogenicity of a Synthetic Oligosaccharide-Protein Conjugate Vaccine against *Haemophilus influenzae* Type b, Infection and Immunity, Dec. 2004, p. 7115-7123 vol. 72, No. 12.

Rettig, Wolfgang, et al., High-Molecular-Weight Glycoproteins of Human Teratocarcinoma Defined by Monoclonal Antibodies to Carbohydrate Determinants, Cancer Research 45, 815-821, Feb. 1985.

Westphal, O, et al., Extraction with Phenol-Water and Further Applications of the Procedure, Methods in Carbohydrate Chemistry, 1965, pp. 83-91.

Yokota, Shin-Ichi, et al., Human Antibody Response to *Helicobacter pylori* Lipopolysaccharide: Presence of an Immunodominant Epitope in the Polysaccharide Chain of Lipopolysaccharide, Infection and Immunity, Jun. 1998, p. 3006-3011 vol. 66, No. 6.

Hiratsuka et al., "Identification of a d-glycero-d-manno-Heptosyltransferase Gene from *Helicobacter pylori*", Journal of Bacteriology, 2005, pp. 5156-5165.

Moran et al., "Role of *Helicobacter pylori* rtaJ genes (HP0159 and HP1416) in lipopolysaccharide synthesis", FEMS Microbiology Letters 241, 2004, pp. 57-65.

\* cited by examiner

K    H    G            F         E             C          B          A
α-Glc-4-β-Gal-7-α-DDHep-2-α-Hep-3-α-Hep7*P*EtN-5-α-Kdo-6-β-GlcN*-6-α-GlcN*1*P*EtN
                                          |2
                                          R

R = H

R = β-GlcNAc (L)

R = α-DDHep-3-α-L-Fuc-3-β-GlcNAc
         N          M          L

R =              heptan                                    glucan

β-GlcNAc-2-α-DDHep-3-[α-DDHep-3-]ₘ-α-DDHep-3-α-DDHep-3-α-Glc-[-6-α-Glc-]ₙ-6-α-Glc-6-
    W           P          T              Y            X          V      Q      Z

-α-DDHep-3-α-L-Fuc-3-β-GlcNAc
     N           M         L

FIG. 3A

K    H    G            F         E          C         B        A
α-Glc-4-β-Gal-7-α-DDHep-2-α-Hep-3-α-Hep6/7*P*-5-α-Kdo-6-β-GlcN-6-GlcNol
                                       |2
                                       R

1: R = H;

2: R = α-GlcN (L)

3: R = α-DDHep-3-α-L-Fuc-3-β-GlcN
          N          M         L

4: R =

β-GlcN-2-α-DDHep-3-[α-DDHep-3-]ₘ-α-DDHep-3-α-DDHep-3-α-Glc-[-6-α-Glc-]ₙ-6-α-Glc-6-
   W         P           T              Y           X        V       Q       Z

-α-DDHep-3-α-L-Fuc-3-β-GlcN-
    N           M         L

FIG. 3B

K  H  G  F  E  C  B
α-Glc-4-β-Gal-7-α-DDHep-2-α-Hep-3-α-Hep6/7P-5-α-Kdo-6-anh-Man-ol    5

α-DDHep-3-[α-DDHep-3-]ₙ-α-DDHep-3-α-DDHep-3-α-Glc-[-6-α-Glc-]-6-α-Glc-6-α-DDHep-3-α-L-Fuc-3-anhMan-ol    6
P     T              Y       X         V      Q     N     M      L

FIG. 3C

α-L-Fuc-3-anhMan-ol    7
M       L

α-Man-3-α-Man-3-α-Man-3-α-Man-3-α-Glc-1-Gro    8
P       T       Y       X       V     K

FIG. 3D

α-Glc-3-α-Glc-4-β-Gal-7-α-DDHep-2-α-Hep-3-α-Hep7P-5-α-Kdo-lipid A
                                |2
              α-Glc-[-6-α-Glc-]ₙ-2-α-DDHep
                                |7
                                R R = [O-chain]-{-3-α-DDHep, -2-α-DDHep, -6-α-DDHep}

FIG. 3E

α-Glc-3-α-Glc-4-β-Gal-7-α-DDHep-2-α-Hep-3-α-Hep7P-5-α-Kdo-lipid A
                                |2
              α-Glc-[-6-α-Glc-]ₙ-2-α-DDHep
                                |7←-{-3-α-DDHep, -2-α-DDHep, -6-α-DDHep}
                      α-Fuc↔β-GlcNAc

FIG. 3F

A
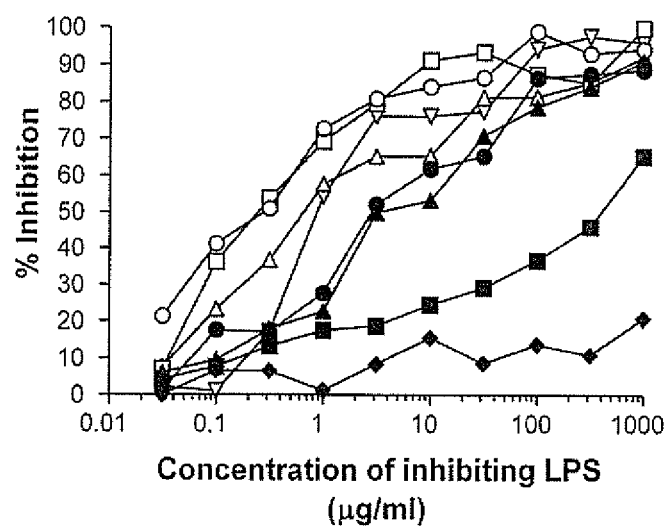
B
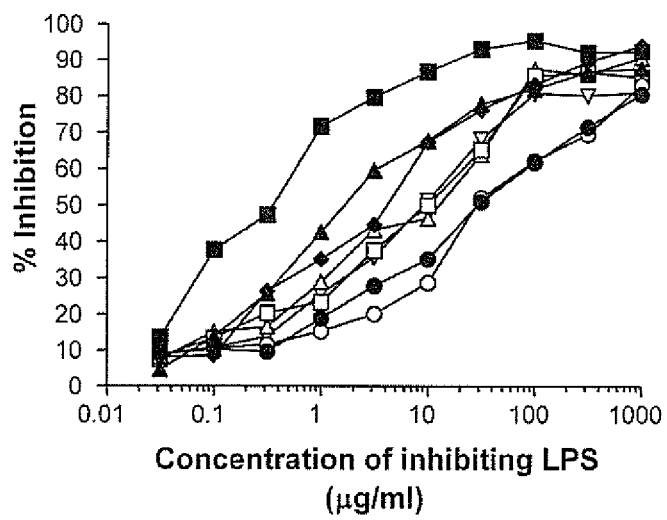
FIG. 6

H. PYLORI LIPOPOLYSACCHARIDE OUTER CORE EPITOPE

PRIOR APPLICATION INFORMATION

The instant application claims the benefit of U.S. Provisional Patent Application 61/230,315, filed Jul. 31, 2009, the entirety of which is incorporated herein by reference.

FIELD OF INVENTION

The present invention relates to a novel *Helicobacter pylori* LPS outer core epitope. More specifically, the present invention relates to a novel *H. pylori* outer core epitope, its synthesis, characterization, and conjugation.

BACKGROUND OF THE INVENTION

*Helicobacter pylori* is recognized as the most common bacterial infection associated with human chronic gastritis, peptic ulcer and gastric carcinoma. *H. pylori* infection has an estimated prevalence of about half the world's population, reaching up to 70% in developing countries and 20-30% in industrialized countries (Dunn et al., 1997). The vast majority of individuals acquire *H. pylori* in childhood; the prevalence of infection among children in developing countries is linked to a low socio-economic status and poor sanitation (Castillo-Rojas et al., 2004). *H. pylori* has been identified by the World Health Organization (WHO) as a class I carcinogen, as it increases the relative risk for gastric cancer at least six-fold. Gastric cancer is the second most common cause of mortality worldwide, and accounts for 700,000 annual deaths (Parkin et al., 2002).

Current eradication strategies of *H. pylori* are based on the use of proton pump inhibitors and antibiotics. However, the efficacy of chemotherapeutic intervention is limited by frequency of antibiotic resistance among *H. pylori* isolates and lack of immunity against re-infection. Thus, novel therapies are needed to provide a global strategy for the prevention and eradication of *H. pylori* infections.

While recent investigations have been focused on the role of protein components in the pathogenesis of *H. pylori* and their role in protective immunity (Ruggiero et al., 2003; Rossi et al., 2004), relatively few studies have explored the possibility of including antigens other than proteins in vaccine formulations (Angelakopoulos and Hohmann, 2000). For example, polysaccharide-based conjugate vaccines are known to prevent systemic infection and inhibit colonization of the host (Anderson et al., 1986; Chu et al., 1991; Pon et al., 1997; Passwell et al., 2001; Passwell et al., 2003). Recent studies of enteric pathogens have examined approaches based on LPS conjugates as candidate vaccines for human use (Gu et al., 1996; Mieszala et al., 2003; Cox et al., 2005; Yu and Gu, 2007).

Lipopolysaccharide (LPS) is a major cell surface component of *H. pylori*. Structural studies carried out on a number of *H. pylori* isolates (Monteiro, 2001) have resulted in a structural model of LPS consisting of an O-chain and a core oligosaccharide that is attached to a lipid A moiety. The structure of the O-chain polysaccharide backbone of most *H. pylori* strains is unique and displays type 2 and/or type 1 Lewis (Le) blood group determinants that mimic those present on the cell surface of human gastric and tumour cells (Wirth et al., 1996); these may be implicated in adverse autoimmune reactions leading to atrophic gastritis (Appelmelk et al., 1996). In addition, the outer core region of *H. pylori* LPS contains two unusual polymeric components: DD-heptoglycan and α1,6-glucan (Monteiro, 2001). The α1,6-glucan polymer in the outer core region *H. pylori* LPS isolates is synthesized by the product of the HP0159 open reading frame. The presence and expression of HP0159 gene in *H. pylori* is common.

A number of *H. pylori* LPS biosynthetic genes have been characterized and their role in pathogenesis and colonization determined (Logan et al., 2000; Logan et al., 2005; Hiratsuka et al., 2005; Chandan et al., 2007; Altman et al., 2008). *H. pylori* HP0826 mutants were constructed and it was demonstrated that this mutation resulted in formation of truncated LPS lacking Le antigen (Logan et al., 2000). However, full characterization of the structure of the LPS was not achieved.

Despite advances in the field, immunogenic epitopes effective across multiple types of *H. pylori* remain elusive.

SUMMARY OF THE INVENTION

The present invention relates to a novel *Helicobacter pylori* LPS outer core epitope. More specifically, the present invention relates to a novel *H. pylori* outer core epitope, its synthesis, characterization, and conjugation.

The present invention provides a α1,6-glucan-containing *Helicobacter pylori* compound comprising the structure of Formula I:

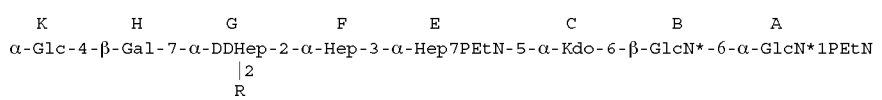

R is a α-DDHep-3-α-L-Fuc-3-β-GlcNAc trisaccharide substituted with an α1,6-glucan linked to an α1,3-DD-heptan, and the last DD-Hep residue of α1,3-DD-heptan is capped with β-GlcNAc residue. In the compound as just described, the α1,6-glucan may comprise from about 3 to about 12 α1,6-linked glucose residues, and the α1,3-DD-heptan may comprise from about 2 to about 6 α1,3-linked heptose residues.

The R group of the compound as described above may be

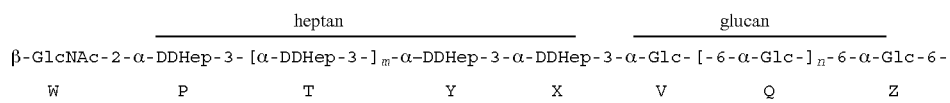

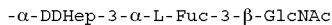

-α-DDHep-3-α-L-Fuc-3-β-GlcNAc
    N         M         L where β-GlcNAc residue L is linked to O-2 of Hep G. In the compound as just described, residues Q and Z of the glucan are α1,6-linked glucose residues, and n may be any value between about 1 to 11; residues T, Y, and X are α1,3-linked heptose residues, and m may be any value between about 0 to 4.

The compound as described above may be isolated or purified from *H. pylori* strain HP0826::Kan.

In the compounds described above, the structure of Formula I may further comprise a lipid A moiety covalently attached to the Kdo residue C. The lipid A molecule may be O-deacylated or may be cleaved through hydrolysis of the ketosidic linkage of the Kdo residue.

The present invention also provides a conjugate, comprising a substantially linear α1,6-glucan-containing compound conjugated to a linker molecule, a protein carrier, or a combination thereof. The substantially linear α1,6-glucan-containing compound may be the compound described herein, wherein the structure of Formula I is conjugated to the linker molecule, protein carrier, or combination thereof. The substantially linear α1,6-glucan-containing compound may alternatively be a Dextran, such as Dextran T5. The protein carrier may be tetanus toxoid or bovine serum albumin.

The present invention also encompasses a composition comprising one or more than one compounds or conjugates as described above.

The present invention further includes an antibody directed against the α1,6-glucan epitope-containing compound described herein. The antibody may be monoclonal antibody 1C4F9. The invention further encompasses hybridoma cell line 1C4F9, which produces monoclonal antibody 1C4F9.

The monoclonal antibody described above may be utilized to cause complement-mediated bacteriolysis of α1,6-glucan-expressing *H. pylori* strains in an individual in need of such treatment.

The present invention also provides the use of an effective amount of the composition described above for inducing an immune response against *H. pylori* in an individual. The compound(s) in the composition may be conjugated to a suitable carrier protein; additionally, the compound(s) in the composition may be conjugated to a suitable carrier protein via a 2-keto-3-deoxy-octulosonic acid (Kdo) of the lipopolysaccharide.

The present invention further provides an immune antiserum produced by immunizing a mammal with the immunogenic composition described herein. The immune antiserum may comprise an IgG recognizing an α1,6-linked glucan epitope in homologous and heterologous typeable and non-typeable mutant and wild-type strains of *H. pylori*. The IgG may cause complement-mediated bacteriolysis of mutant and wild-type α1,6-glucan-expressing *H. pylori* strains.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 1A shows the extracted mass spectrum (m/z 1000-1500), while FIG. 1B shows the product ion spectrum of ions at m/z 1266.3.

FIG. 2A shows the extracted mass spectrum (m/z 600-2000), while FIG. 2B shows product ion spectrum of ions at m/z 1597.7. Fragment ions corresponding to the lipid A moiety are marked with asterisk.

FIG. 3A shows the structure of the major LPS glycoform from *H. pylori* strain 26695 HP0826::Kan; acylation is not shown. Products of the KOH deacylation of the LPS of FIG. 3A are shown in FIG. 3B (compounds 1 to 4). Products of the deamination of compound 4 are shown in FIG. 3C (compounds 5 and 6). Products of the periodate oxidation of compound 6 are shown in FIG. 3D (compounds 7 and 8). Structures previously proposed in the art for *H. pylori* LPS from strain 26695 (FIG. 3E) and *H. pylori* LPS from strain 26695 HP0826::Kan mutant (FIG. 3F) are also shown (adapted from Logan et al., 2000). PEtn=phosphoethanolamine; Glc=D-glucopyranose; Gal=D-galactopyranose; Kdo=2-keto-3-deoxy-octulosonic acid; LDHep=L-glycero-D-manno-heptose; DDHep=D-glycero-D-manno-heptose; GlcNAc=2-acetamido-2-deoxy-D-glucose; GlcN=2-amino-2-deoxy-D-glucose; Fuc=L-fucose; P=phosphate; and Gro=glycerol.

FIG. 6 shows graphs for the determination of the specificity of rabbit antibodies elicited by dLPS-TT conjugate by inhibition ELISA with *H. pylori* LPS from 26695 HP0479::Kan (FIG. 6A) and 26695 HP0826::Kan (FIG. 6B). Coating LPS are depicted as follows: filled squares—26695; filled diamonds—26695 HP0826::Kan; filled circle—26695 HP0159::Kan; filled triangles—26695 HP0479::Kan; open circles—SS1; open squares—SS1 HP0826::Kan; open triangles—SS1 HP0159::Kan; open inverted triangles—SS1 HP0479::Kan;

DESCRIPTION OF THE PREFERRED EMBODIMENTS

Figure 1:
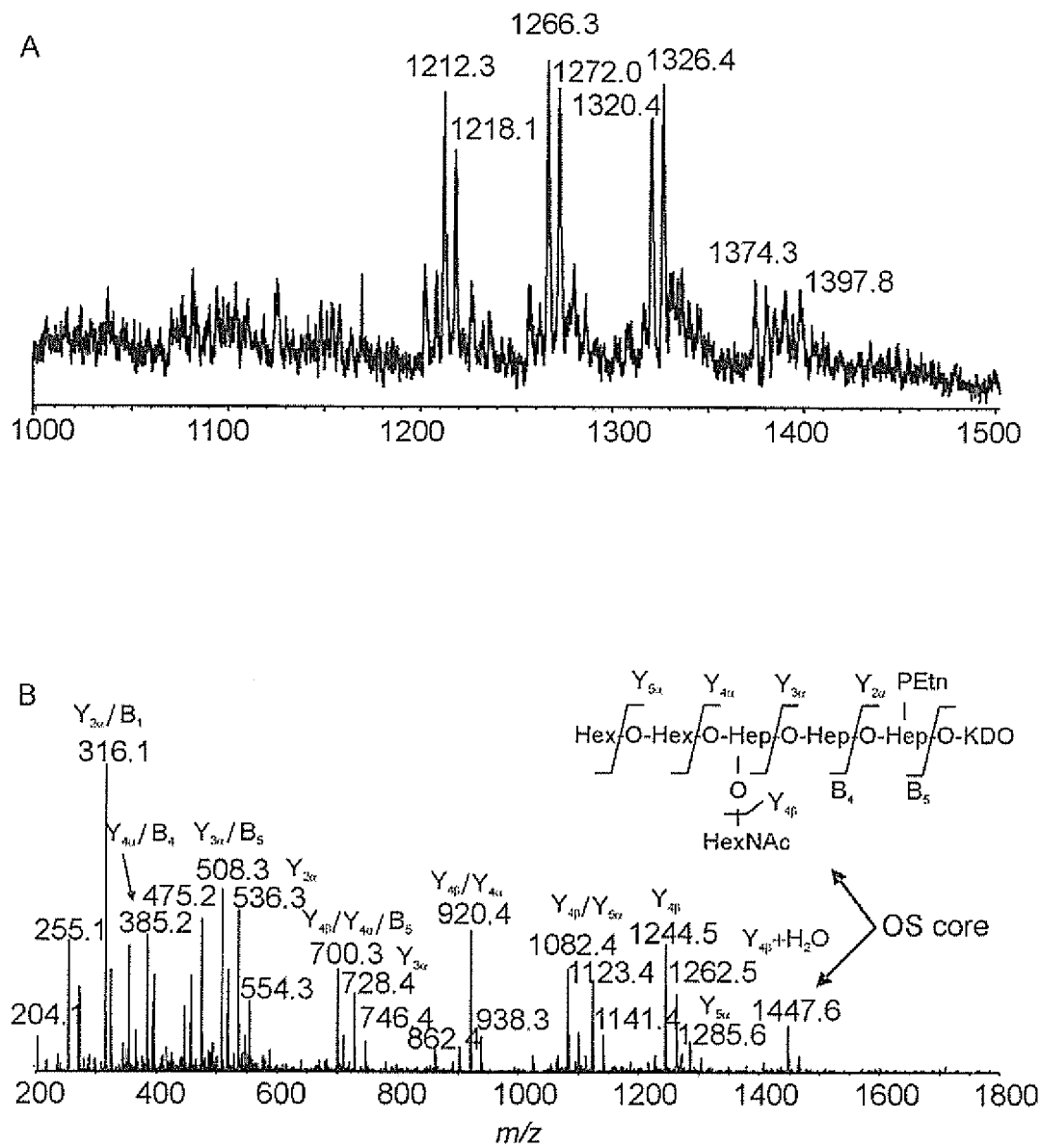
FIG. 1 shows a CE-MS analysis of LPS glycoforms in fraction 1 of the delipidated LPS from *H. pylori* strain 26695 HP0826::Kan in the positive ion mode.

The present invention relates to a novel *Helicobacter pylori* LPS outer core epitope. More specifically, the present invention relates to a novel *H. pylori* outer core epitope, its synthesis, characterization, and conjugation.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, 'purified' does not necessarily mean absolute purity but rather is intended as a relative definition. Similarly, as used herein, 'isolated' refers to the removal of something from its native environment.

*Helicobacter pylori* is a bacterial pathogen commonly associated with human chronic gastritis, peptic ulcer and gastric carcinoma; as a result of the increased risk of gastric cancer associated with *H. pylori* infection, it has been classified as a class I carcinogen. Lipopolysaccharide (LPS) is a major cell surface component of *H. pylori*. Prior publications relating to structural studies of *H. pylori* LPS led to a proposed model where an O-chain polysaccharide is covalently linked to a core oligosaccharide, which is in turn attached to a lipid A moiety. The O-chain polysaccharide backbone of most *H. pylori* strains is unique and can display type 2 and/or type 1 Lewis (Le) blood group determinants; this polysaccharide component is antigenic. "Typeable" *H. pylori* strains have Lewis epitopes (Le X and/or Le Y antigens) that can be recognized by anti-Lewis antibodies (anti-Le); such antibodies may be commercially available and assist in typing. "Non-typeable" strains do not contain Lewis structures.

Further structural studies established that the outer core region of *H. pylori* LPS contains two unusual polymeric components: DD-heptoglycan and α1,6-glucan side chains (Monteiro, 2001). Logan et al. (2000) also provided insight regarding the structure of the LPS. Specifically, the proposed structures (see FIGS. 3E and 3F) provided that the DD-heptose (DD-Hep) in the side chain is attached to the DD-Hep in the backbone, while the α1,6-glucan is attached to this side-chain DD-Hep and forming another branch. Specifically, Logan et al. (2000) determined the length of the glucan chain in 0826 mutant LPS to be one to three glucoses based on FAB-MS spectra (fast atom bombardment mass spectrometry). Presence of α1,6-linked glucose in *H. pylori* strain 26695 LPS was also described and was based on the methylation analysis data, but the length of the glucan was not determined. It was additionally suggested that in strain 26695 LPS, 3-substituted Hep forms a connection between GlcNAc unit of the O-chain and the core. Presence of 3-linked heptose in *H. pylori* HP0826::Kan LPS was also stated, but the presence of α1,3-heptan or its length were not described. No further information regarding the structure or length of the heptan or glucan side chains were provided. The structure of *H. pylori* LPS is presently further defined.

The present invention provides a novel α1,6-glucan-containing *Helicobacter pylori* compound comprising the structure of Formula I:

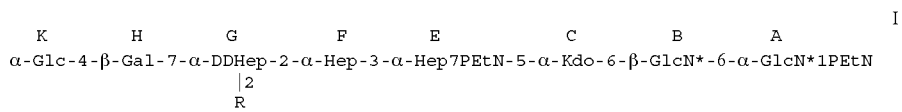

$$\begin{array}{cccccccc} K & H & G & F & E & C & B & A \\ \alpha\text{-Glc-4-}\beta\text{-Gal-7-}\alpha\text{-DDHep-2-}\alpha\text{-Hep-3-}\alpha\text{-Hep7PEtN-5-}\alpha\text{-Kdo-6-}\beta\text{-GlcN*-6-}\alpha\text{-GlcN*1PEtN} \\ & & & |2 & & & & \\ & & & R & & & & \end{array}$$

wherein R is a α-DDHep-3-α-L-Fuc-3-O-GlcNAc trisaccharide substituted with an α1,6-glucan followed by α1,3-DD-heptan, where the last DD-Hep residue of α1,3-DD-heptan is capped with j-GlcNAc residue.

In the structure as described above, the β-GlcNAc of the trisaccharide (α-DDHep-3-α-L-Fuc-3-O-GlcNAc), is linked to α-DDHep G. The α-DDHep of the trisaccharide is linked to the α1,6-glucan, which is in turn linked to the α1,3-DD-heptan. The α1,3-DD-heptan is then linked to a β-GlcNAc residue; the latter may provide a point of attachment for the O-chain polysaccharide. By the term "linked" or "substituted", it is meant that the two moieties are joined by a covalent bond.

The term "α1,6-glucan" used herein may also be referred to interchangeably as "glucan", "α1,6-glucan side chain", "glucan side chain", "α1,6-glucan moiety", and/or "glucan moiety". The α1,6-glucan is a linear polysaccharide chain of glucose monomers linked by α1,6 O-glycosidic bonds. In one example, which is not intended to be limiting in any manner, the α1,6-glucan may be a linear polysaccharide. The α1,6-glucan may comprise any suitable amount of α1,6-glucose residues. For example, and without wishing to be limiting in any manner, the glucan may comprise from about 3 to about 12 α1,6-linked glucose residues; specifically, the glucan moiety may comprise about 3, 4, 5, 6, 7, 8, 9, 10, 11 or 12 α1,6-linked glucose residues, or any range defined by any two values just recited.

In one non-limiting example, the α1,6-glucan may comprise 9-12 α1,6-glucose residues; in another non-limiting example, the α1,6-glucan may comprise 10 α1,6-glucose residues.

The term "glycoform" as used herein indicates different forms or types of the compound with the same LPS structure but differing in a number of α1,6-glucose or α1,3-heptose residues. For example, and without wishing to be bound by theory, each glycoform may comprise a specific length glucan and/or heptan moiety or a combination of thereof.

The term "α1,3-heptan" used herein may also be referred to interchangeably as "α1,3-DD-heptan", "heptan", "α1,3-heptan side chain", "heptan side chain", "α1,3-heptan moiety", "heptan moiety", and/or "DD-heptoglycan". The α1,3-heptan is a polysaccharide chain of heptose monomers linked by α1,3 O-glycosidic bonds. In one example, which is not intended to be limiting in any manner, the α1,3-heptan may be a linear polysaccharide. The α1,3-heptan may comprise any suitable amount of α1,3-heptose residues. For example, and without wishing to be limiting in any manner, the heptan may comprise from about 2 to about 6 α1,3-linked heptose residues; specifically, the heptan moiety may comprise about 2, 3, 4, 5, or 6 α1,3-linked heptose residues, or any range defined by any two values just recited.

The last DD-Hep residue of the α1,3-DD-heptan described above is capped with a f-GlcNAc residue. By the term "capped", it is meant that the β-GlcNAc residue is the last residue in the side-chain; the term "terminated" may also be used. The β-GlcNAc may be linked to the DD-Hep via position O-2 of the heptose. Without wishing to be bound by theory, the β-GlcNAc residue may provide a point of attachment for the O-chain polysaccharide.

In one non-limiting example, R may be

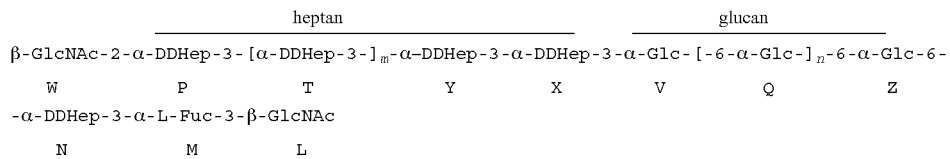

where β-GlcNAc residue L is linked to O-2 of Hep residue G. In this example, the β-GlcNAc residue W may provide a point of attachment for the O-chain polysaccharide. In the compound as just described, residues Q and Z of the glucan are α1,6-linked glucose residues, and n may be any value between about 1 to 11, such that the glucan comprises from about 3 to about 12 glucose residues in α1,6-linkage; in one specific, non-limiting example, a major glycoform contains 10 consecutive α1,6-linked glucose residues (n=9). In the compound as just described, residues T, Y, and X are α1,3-linked heptose residues, and m may be any value between about 0 to 4, such that the heptan comprises from about 2 to about 6 heptose residues in α1,3-linkage; in one specific, non-limiting example, a major glycoform contains 4 consecutive α1,3-linked heptose residues (m=2).

The structure may be isolated and/or purified from any suitable *H. pylori* strain; for example, and without wishing to be limiting in any manner, the truncated *H. pylori* LPS molecule may be isolated from a non-typeable *H. pylori* strain (i.e., one devoid of Lewis antigens), such as and not limited to a *H. pylori* strain having mutation in HP0826 gene leading to an isogenic mutant lacking O-chain polysaccharide. In a non-limiting example, the compound described herein may be isolated and/or purified from *H. pylori* strain 26695 HP0826::Kan or strain PJ2.

The structure of Formula I, also referred to herein as the "inner core molecule", may further comprise a lipid A moiety covalently attached to a Kdo residue, for example the Kdo residue C. In other embodiments, the lipid A molecule may be O-deacylated or may be completely deacylated. In yet other embodiments, lipid A moiety may be cleaved through hydrolysis of the ketosidic linkage of the Kdo residue. Without wishing to be bound by theory, the cleavage of lipid A may be done to eliminate the toxicity of LPS and to avoid possible aggregation and insolubility of the conjugate. Persons of skill in the art would be familiar with methods for O-deacylation, deacylation, or hydrolysis of the ketosidic linkage of the lipid A moiety (see for example, Holst et al., 1991; Altman et al., 2003).

The present invention also provides a conjugate comprising a substantially linear α1,6-glucan-containing compound conjugated to a protein carrier. The substantially linear α1,6-glucan-containing compound may be any suitable substantially linear polysaccharide comprised of α1,6-linked glucose residues. By the term "substantially linear", it is meant that the α1,6-glucan contains few branches; for example, and without wishing to be limiting in any manner, the α1,6-glucan may comprise from about 0 to about 5% branching in the α1,6-glucan. Specifically, the α1,6-glucan may comprise about 0, 0.5, 1, 1.5, 2, 2.5, 3, 3.5, 4, 4.5, or 5% branching, or any amount therebetween; the compound may also be a mixture, wherein the amount of branching within the mixture varies from one compound to another. In one non-limiting example, the α1,6-glucan-containing compound may be the structure as described above and herein. In another example, the α1,6-glucan-containing compound may be a Dextran. The Dextran may be any suitable Dextran that meets the requirements described above and having a molecular weight of between 1 and 10 kDa; for example but without wishing to be limiting in any manner, the Dextran may be about 1, 3.5, 5, 6.5, 8, or 10 kDa, or any value therebetween. In a specific, non-limiting example, the Dextran may be Dextran T5. In yet another example, the α1,6-glucan-containing compound may be a linear chain of between about 5 and 8 α1,6-linked glucose residues; for example, and without wishing to be limiting in any manner, the α1,6-glucan-containing compound may be a linear chain of 5, 6, 7, or 8 α1,6-linked glucose residues.

Figure 4:
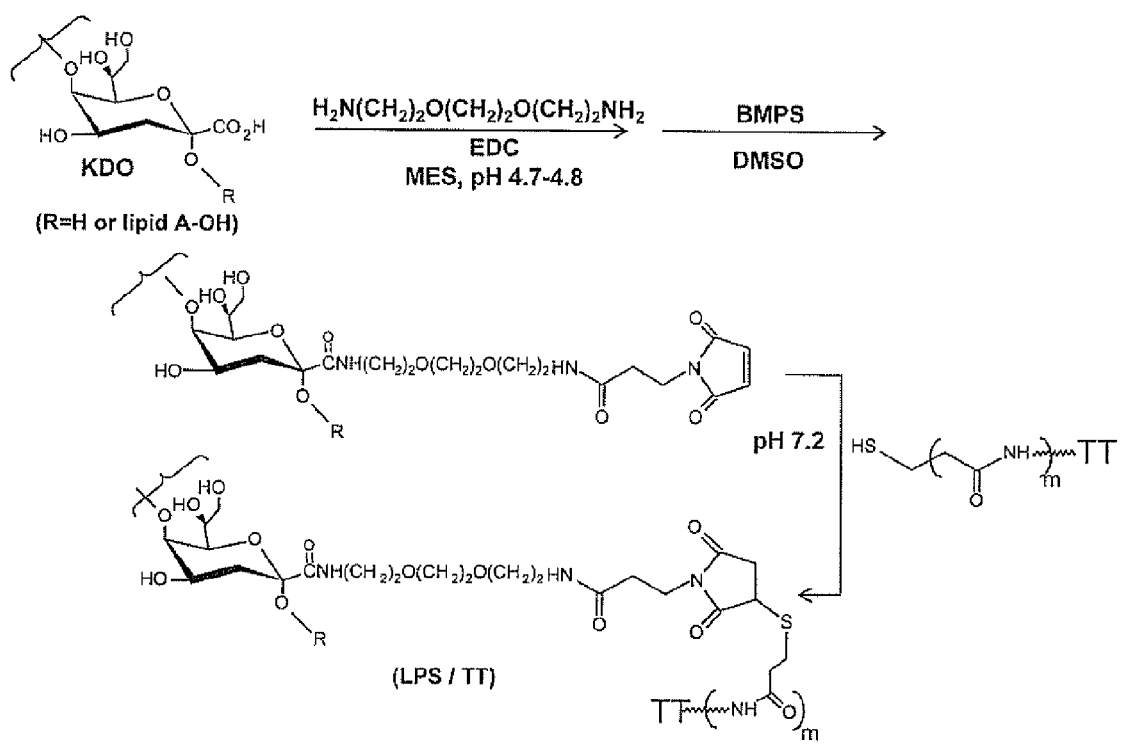
FIG. 4 shows a reaction scheme for the preparation of LPS-based conjugates of the present invention.

The α1,6-glucan-containing compound is conjugated to a linker molecule and/or a carrier protein; as would be understood by one of skill in the art, the structure described herein may be directly conjugated to the carrier protein, or may be conjugated to a linker molecule (also referred to herein as "linker") that is in turn conjugated to the carrier protein. By the term "conjugated", it is meant that the structure is covalently attached or linked to the linker molecule and/or carrier protein. Methods for covalent attachment of the linker and/or carrier protein are well-known to those of skill in the art; as would be appreciated by the skilled person, the method for covalent attachment (and whether or not a linker is present) may vary based on the carrier protein used. Without wishing to be limiting in any manner, one such method is shown in FIG. 4, which is adapted from Fernandez-Santana et al. (1998); in this method, deacylated or delipidated LPS is activated by covalently linking the carboxyl group of a Kdo residue to a linker molecule, followed by the introduction of a maleimido functionality. The activated LPS is mixed with thiolated carrier protein to produce a conjugated structure. As will be appreciated by one of skill in the art, the method described herein is general and accordingly any other suitable method may be used (for example, but not limited to those described by Chu et al., 1991; Cox et al., 2005; Gu et al., 1996; Mieszala et al., 2003; Yu and Gu, 2007). The α1,6-glucan-containing compound may be attached to the linker/carrier protein via a carboxyl group of any suitable carbohydrate residue in the structure. In a specific, non-limiting example, the α1,6-glucan-containing compound may be the structure of the present invention and may be attached via the inner core Kdo residue C.

The carrier protein may be any suitable carrier known in the art, including immunogenic carriers. For example, the carrier protein may be, but is not limited to tetanus toxoid, serum bovine albumin (BSA), Diphteria toxoid, mutant Diphteria toxoid, CRM, $CRM_{197}$ protein, *Pseudomonas* A protein, Cholera toxin (CT) protein, a Cholera toxin mutant CT-E29H protein, and others known in the art for example but by no means limited to parts of flagella, pili and other toxins.

As previously indicated, conjugates could be prepared by either directly connecting the carrier protein and the structure of the present invention via naturally occurring groups or connecting via introduction of spacer or linker molecules, comprising but by no means limited to primary amino groups, hydrazides, thiols, carboxyls and others.

The present invention additionally provides a composition comprising one or more compounds as described herein, one or more conjugate as described herein, or a combination thereof. In one embodiment, the composition may comprise a mixture of glycoforms of the compound described above; for example, and without wishing to be limiting in any manner, the composition may comprise a major glycoform comprising 10 consecutive α1,6-linked glucose residues (n=9) in the glucan moiety. Similarly, and without wishing to be limiting in any manner, a composition could comprise conjugates prepared from more than one glycoform described herein. As demonstrated in the Examples, the LPS structure elaborated by *H. pylori* strain 26695 HP0826::Kan that was used for preparation of conjugates was a mixture of three glycoforms: backbone oligosaccharide I, backbone oligosaccharide I capped with GlcNAc and [GlcNAc, Fuc, Hep], and oligosaccharide containing α1,6-linked glucan, with the longest glucan chain corresponding to approximately twelve α1,6-linked residues, as determined by CE-MS analysis (Table 2, FIG. 2).

The composition as just described may be immunogenic. By the term "immunogenic", it is meant that the composition may induce an immune response against *H. pylori* wild-type and/or mutant strains. The immune response may provide a broad immunogenic response against typeable and non-typeable strains of *H. pylori*.

The present invention also provides a use of an effective amount of the composition as described herein for inducing an immune response against *H. pylori* in an individual. As previously described, the composition may comprise one or more than one compound in accordance with the present invention. The one or more than one compound may be conjugated to a linker and/or a suitable carrier molecule.

The present invention further provides an immune antiserum produced by immunizing a mammal with the immunogenic composition as described above. The immune antiserum may comprise or yield a post-immune serum IgG recognizing an α1,6-linked glucan epitope in homologous and heterologous typeable and non-typeable mutant and wild-type strains of *H. pylori*. The IgG may cause complement-mediated bacteriolysis of mutant and wild-type α1,6-glucan-expressing *H. pylori* strains.

Figure 5:
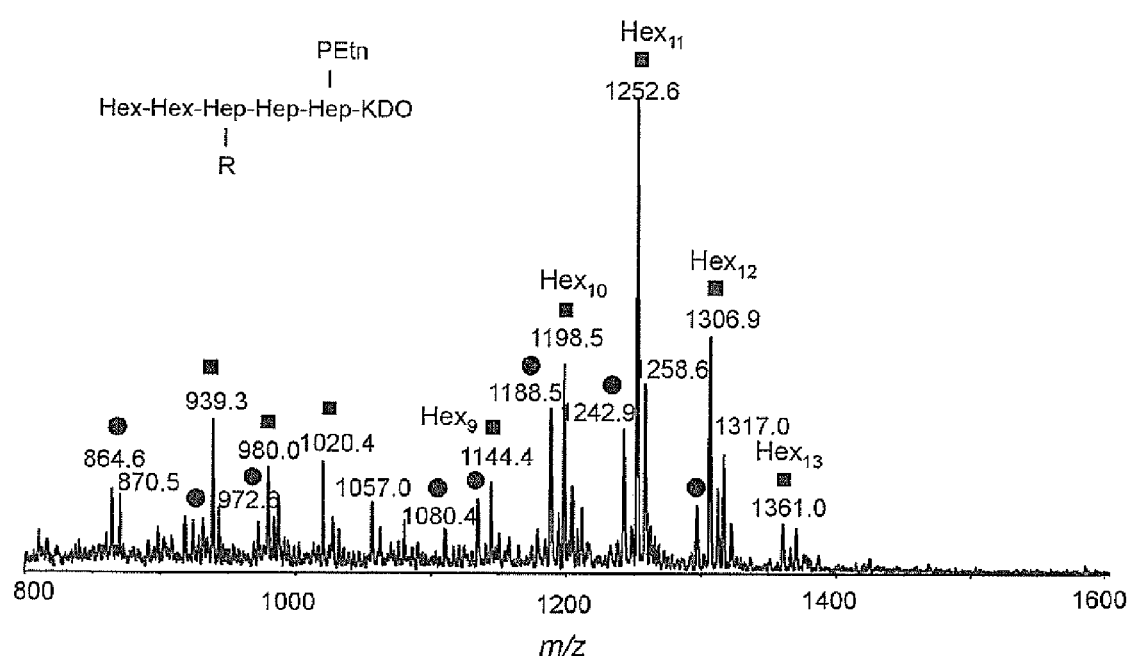
FIG. 5 shows a CE-MS analysis of the major fraction of the delipidated *H. pylori* O:3 HP0826::Kan LPS in the negative ion mode. ●: LPS glycoforms containing one Hep residue in the side chain, R=Hex$_{5-13}$, Hep, HexNAc, Fuc; ■: LPS glycoforms containing two Hep residues in the side chain, R=Hex$_{8-13}$, Hep, Hep, HexNAc, Fuc.

The present invention additionally provides anti-α1,6-glucan antibodies. The antibodies may be raised against the compound of the invention as described herein, or may be raised against other α1,6-glucan-containing molecules such as Dextran (or Dextran conjugates, for example but not limited to BSA-Dextran conjugates). In one non-limiting example, the antibody may be a monoclonal antibody, produced according to methods known in the art (see Example 10; Altman at al., 2005). For example, and without wishing to be limiting in any manner, the antibody may be a monoclonal antibody, raised against the α1,6-glucan epitope present in the outer core region of *H. pylori* HP0826 mutant LPS; more specifically, the antibody may be raised against the compound shown in FIG. 5. In yet a more specific example, the monoclonal antibody may be IgM 1C4F9, produced by hybridoma cell line 1C4F9. This cell line has been deposited with the International Depositary Authority of Canada (National Microbiology Laboratory, Public Health Agency of Canada, 1015 Arlington Street, Winnipeg, Manitoba, CANADA) on Jul. 30, 2009 and assigned accession number 300709-01 As demonstrated in the examples, 1C4F9 recognized the α1,6-glucan epitope in LPS and whole cells of typeable and non-typeable *H. pylori* strains, was readily accessible on the surface of live bacteria, and reacted equally well with both LPS-OH-TT and dLPS-BSA or dLPS-TT conjugates.

The present invention provides the use of 1C4F9 antibody to cause complement-mediated bacteriolysis of mutant and wild-type typeable and non-typeable α1,6-glucan-expressing *H. pylori* strains in an individual in need of such treatment. As previously described, typeable *H. pylori* strains have Lewis antigens recognized by anti-Le antibodies while non-typeable strains do not. However, since both typeable and non-typeable strains contain α1,6-glucan, both types of strains will be recognized by 1C4F9 antibody.

Currently in the art, *H. pylori* strains may be typed using commercially available antibodies against Lewis antigens; however, as non-typeable strains do not contain Lewis structures, they cannot be classified using this approach. As most typeable and non-typeable *H. pylori* strains carry α1,6-glucan epitopes, anti-α1,6-glucan antibodies (such as mAb 1C4F9) could provide an additional method of screening and characterizing *H. pylori* isolates.

The LPS of *H. pylori* strain 26695 HP0826::Kan was purified and its chemical structure determined by composition, methylation, in-depth nuclear magnetic resonance (NMR) analysis, as well as CE-MS data. The presence of α1,6-linked glucan in the outer core region of *H. pylori* HP0826 mutant LPS was also demonstrated; this structure was recognized by α1,6-glucan-specific monoclonal antibody, 1C4F9. The latter antibody was generated using formalin-fixed cells of *H. pylori* 0:3 HP0826::Kan mutant strain. These antibodies were cell-surface accessible and bactericidal. Previously, it was believed that only the Lewis structures were antigenic; thus, the generation of antibodies against α1,6-glucan was unexpected.

To investigate the vaccine potential of *H. pylori* LPS, modified LPS of *H. pylori* 26695 HP0826::Kan mutant, was conjugated to tetanus toxoid (TT) or bovine serum albumin (BSA). Two approaches for preparation of the partially delipidated or delipidated LPS were utilised: O-deacylation of LPS by mild hydrazinolysis (LPS-OH) or delipidation of LPS by mild acid treatment (dLPS). Additional methods of delipidation and/or partial delipidation are well known in the art and such suitable methods may be used within the scope of the present invention. Both LPS-OH and dLPS were covalently linked through a 2-keto-3-deoxy-octulosonic acid (Kdo) residue to a diamino group-containing spacer, followed by the introduction of a maleimido functionality and conjugation to thiolated TT or BSA to give conjugates LPS-OH-TT, dLPS-BSA and dLPS-TT, respectively. In a separate experiment, non-typeable strain PJ2 was delipidated and utilised for conjugation to give dLPS(PJ2)-TT conjugate.

The LPS-OH-TT, dLPS-BSA, dLPS-TT conjugates as well as dLPS(PJ2)-TT retained antigenicity of the surface accessible α1,6-glucan determinant, as established by indirect ELISA with IgM 1C4F9. The antibody was shown to have excellent specificity for the α1,6-glucan determinant and its binding characteristics were determined by inhibition ELISA with oligosaccharides from isomalto-series and purified LPS from typeable and non-typeable strains of *H. pylori*.

These studies confirmed that 1C4F9 had a requirement for 5 to 6 consecutive α1,6-linked glucose residues, a pattern consistent with the size of anti-α-(1→6)dextran combining sites postulated by Kabat (1993).

The LPS-OH-TT, dLPS-BSA, dLPS-TT or dLPS(PJ2)-TT conjugates were immunogenic in mice and rabbits and induced significant IgG antibody responses to LPS from homologous, heterologous, and wild-type strains of *H. pylori*. A ten-fold stronger IgG immune response to the immunizing antigen was generated in mice and rabbits that received dLPS-containing conjugate. The post-immune sera of rabbits immunized with either LPS-OH-TT, dLPS-BSA, dLPS-TT or dLPS(PJ2)-TT displayed bactericidal activity against 26695 HP0826::Kan mutant and the wild-type 26695 strains of *H. pylori*.

In summary, these results indicate that delipidated or partially delipidated *H. pylori* LPS-based protein conjugates devoid of Le antigen and carrying a long α1,6-glucan chain are immunogenic in both mice and rabbits and induce bactericidal antibodies. It is important to note that this epitope has been identified as being immunogenic. This was not established previously as only Lewis structures were known to be antigenic and to produce specific antibodies.

The present invention will be further illustrated in the following examples. However, it is to be understood that these examples are for illustrative purposes only and should not be used to limit the scope of the present invention in any manner.

Example 1

Isolation and Structural Analysis of *H. pylori* 26696 HP0826::Kan LPS

*Helicobacter pylori* strain 26695 was obtained from Dr. R. Alm (Astra Zeneca, Boston, Mass.), *H. pylori* 0:3 isolate was from Dr. J. Penner, J99 was obtained from Dr. D. Taylor (University of Alberta, Edmonton, Canada), SS1 from Dr. A. Lee (The University of New South Wales, Sydney, Australia), PJ1 and PJ2 clinical isolates were fresh clinical isolates from Dr. W. Conlan (IBS, NRC) and M6 was from Dr. K. Eaton (Michigan State University, MI).

Growth of bacterial strains was carried out as described by Hiratsuka et al. (2005). Briefly, cells were grown at 37° C. on antibiotic-supplemented Columbia blood agar (DIFCO™) plates containing 7% horse blood in microaerophilic environment for 48 h (Kan 20 µg/mL) as previously described (Hiratsuka et al., 2005). For growth in liquid culture, antibiotic supplemented *Brucella* broth containing 10% fetal bovine serum was inoculated with *H. pylori* cells harvested from 48 h Columbia blood agar/horse blood plates and incubated for 48 h in a shaker under microaerophilic conditions (85% $N_2$, 10% $CO_2$, 5% $O_2$) as previously described (Hiratsuka et al., 2005).

*H. pylori* strains were cultivated in liquid culture as described above, and the wet cell mass obtained by centrifugation of the bacterial growth was washed twice successively with ethanol, acetone and light petroleum ether and air-dried. LPS was extracted from the air-dried cellular mass by hot phenol-water extraction procedure of Westphal and Jann (1965). LPS was obtained from the aqueous phase after extensive dialysis and lyophilization. *H. pylori* LPS was further purified by ultracentrifugation (105,000×g, 4° C., 12 h), and the pellet was suspended in distilled water and lyophilized.

Sugar composition analysis was performed by the alditol acetate method (Sawardeker et al., 1967). The hydrolysis was done in 4 M trifluoroacetic acid at 100° C. for 4 h or 2 M trifluoroacetic acid at 100° C. for 16 h followed by reduction in $H_2O$ with $NaBH_4$ and subsequent acetylation with acetic anhydride/pyridine. Alditol acetate derivatives were analyzed as previously described (Altman et al., 2003). Methylation analysis was carried out according to the method of Ciucanu & Kerek (1984) and with characterization of permethylated alditol acetate derivatives by gas liquid chromatography-mass spectrometry (GLC-MS) as previously described (Altman et al., 2003).

Sugar analysis of purified LPS from *H. pylori* 26695 HP0826::Kan as alditol acetates revealed the presence of L-fucose (L-Fuc), D-glucose (D-Glc), D-galactose (D-Gal), N-acetyl-D-glucosamine (D-GlcNAc), D-glycero-D-manno-heptose (DD-Hep) and L-glycero-D-manno-heptose (LD-Hep) in the approximate molar ratio of 0.4:5.0:1.5:4.3:6.4:1.4, indicating the presence of the structure devoid of O-chain (Logan et al., 2000). Methylation analysis carried out on the intact 26695 HP0826::Kan LPS was consistent with these findings and showed the presence of terminal L-Fuc, 3-substituted L-Fuc, terminal D-Glc, terminal D-Gal, 3-substituted glucose, 4-substituted D-Gal, 6-substituted glucose, terminal DD-Hep, 2-substituted DD-Hep, 6-substituted DD-Hep, 3-substituted DD-Hep, 7-substituted DD-Hep, 2,7-substituted DD-Hep, 2-substituted LD-Hep, 3-substituted LD-Hep, terminal D-GlcNAc and 3-substituted D-GlcNAc in the approximate molar ratio of 0.1:1.0:1.1:0.1:1.2:1.0:6.0:0.4:1.2:1.1:3.1:0.5:1.6:1.2:0.1:0.3:0.4. No 3,4-substituted D-GlcNAc and 2-linked D-Gal, characteristic of the O-chain containing Le antigens, were detected. The purity of LPS was confirmed by the absence of RNA derived ribitol. Composition and methylation analyses of 26695 LPS have been reported elsewhere (Logan et al., 2005). All sugars were present in the pyranose form.

Example 2

Characterization of Delipidated *H. pylori* 26695 HP0826::Kan LPS by Capillary Electrophoresis-Mass Spectrometry (CE-MS)

Purified 26695 HP0826::Kan LPS (20 mg) obtained in Example 1 was hydrolyzed in 0.1 M sodium acetate buffer, pH 4.2, for 2 h at 100° C. and fractionated by gel filtration on a BIO-GEL™ P-2 column as described previously (Altman et al., 2003) to generate delipidated LPS (dLPS). Three fractions (fractions 1-3) were collected and analyzed by capillary electrophoresis mass spectrometry (CE-MS; Table 1).

For CE-MS, a PRINCE™ CE system (Prince Technologies, The Netherlands) was coupled to a 4000 QTRAP™ mass spectrometer (Applied APPLIED BIOSYSTEMS™/MDS SCIEX™, Canada). A sheath solution (isopropanol-methanol, 2:1) was delivered at a flow rate of 1.0 µL/min. Separations were obtained on about 90 cm length bare fused-silica capillary using 15 mM ammonium acetate in deionized water, pH 9.0. The 5 kV electrospray ionization voltage was used for the positive ion detection mode. Tandem mass spectra were obtained using enhanced production ion scan mode (EPI) with a scan rate of 4000 Da/s. Nitrogen was used as curtain (at a value of 12) and collision gas (set to scale "high").

CE-MS analysis of the major fraction 1 in the positive ion mode confirmed the presence of a series of triply charged ions at m/z 1212.3, m/z 1266.3 and m/z 1320.4 consistent with consecutive additions of Hex residues, the longest glucan chain corresponding to approximately eleven α1,6-linked residues. Based on the signal intensity of ions, the most abundant glycoform at m/z 1266.3 contained ten α-1,6-linked Hex (FIG. 1). Product ion spectrum of ions at m/z 1266.3 in the positive ion detection mode confirmed the presence of diagnostic ions at m/z 1244.5 and m/z 1447.6 consistent with the previously observed backbone core fragments $Hex_2 Hep_3$ (PEtn)Kdo and $HexNAcHex_2 Hep_3$ (PEtn)Kdo, respectively (FIG. 1). Fractions 1 and 2, carrying α1,6-glucan in the LPS core, were combined and used for conjugation.

CE-MS analysis of the O-deacylated 26695 HP0826::Kan LPS (LPS-OH) in the positive ion mode was performed as described in Example 2. Results of CE-MS were consistent with MS data obtained for delipidated LPS and afforded three major doubly charged ions at m/z 1137.2, m/z 1239.2 and m/z 1408.0 consistent with the presence of the backbone oligosaccharide and backbone oligosaccharide capped with HexNAc

TABLE 1

Positive-ion CE-MS data and proposed composition of LPS glycoforms in delipidated LPS from *H. pylori* strain 26695 HP0826::Kan.

| Pooled fraction | Observed ion (m/z) | Molecular mass (Da) Observed | Calculated[a] | Proposed composition[b] |
|---|---|---|---|---|
| Fraction 1 | $[M + H + 2NH_4]^{3+}$ | | | |
| | 1212.3 | 3599.9 | 3599.1 | $Hex_{12} Hep_5 PEtn_1 HexNAc_1 Fuc_1$ anhydroKDO$_1$ |
| | 1218.1 | 3617.3 | 3617.1 | $Hex_{12} Hep_5 PEtn_1 HexNAc_1 Fuc_1 KDO_1$ |
| | 1266.3 | 3761.9 | 3761.2 | $Hex_{13} Hep_5 PEtn_1 HexNAc_1 Fuc_1$ anhydroKDO$_1$ |
| | 1272.0 | 3779.0 | 3779.2 | $Hex_{13} Hep_5 PEtn_1 HexNAc_1 Fuc_1 KDO_1$ |
| | 1320.4 | 3924.2 | 3923.4 | $Hex_{14} Hep_5 PEtn_1 HexNAc_1 Fuc_1$ anhydroKDO$_1$ |
| | 1326.4 | 3942.2 | 3941.4 | $Hex_{14} Hep_5 PEtn_1 HexNAc_1 Fuc_1 KDO_1$ |
| Fraction 2 | $[M + H + NR_4]^{2+}$ | | | |
| | 902.4 | 1785.8 | 1785.5 | $Hex_2 Hep_4 PEtn_1 HexNAc_1 Fuc_1$ anhydroKDO$_1$ |
| | 911.4 | 1803.8 | 1803.5 | $Hex_2 Hep_4 PEtn_1 HexNAc_1 Fuc_1 KDO_1$ |
| | 983.5 | 1948.0 | 1947.7 | $Hex_3 Hep_4 PEtn_1 HexNAc_1 Fuc_1$ anhydroKDO$_1$ |
| | 992.5 | 1966.0 | 1965.7 | $Hex_3 Hep_4 PEtn_1 HexNAc_1 Fuc_1 KDO_1$ |
| | 1064.6 | 2110.2 | 2109.8 | $Hex_4 Hep_4 PEtn_1 HexNAc_1 Fuc_1$ anhydroKDO$_1$ |
| | 1073.6 | 2128.2 | 2127.8 | $Hex_4 Hep_4 PEtn_1 HexNAc_1 Fuc_1 KDO_1$ |
| | 1145.5 | 2272.0 | 2271.9 | $Hex_5 Hep_4 PEtn_1 HexNAc_1 Fuc_1$ anhydroKDO$_1$ |
| | 1154.5 | 2290.0 | 2290.0 | $Hex_5 Hep_4 PEtn_1 HexNAc_1 Fuc_1 KDO_1$ |
| Fraction 3 | $[M + H + NH_4]^{2+}$ | | | |
| | 631.6 | 1244.2 | 1244.0 | $Hex_2 Hep_3 PEtn_1$ anhydroKDO$_1$ |
| | 640.6 | 1262.2 | 1262.0 | $Hex_2 Hep_3 PEtn_1 HexNAc_1 KDO_1$ |
| | 733.2 | 1447.4 | 1447.2 | $Hex_2 Hep_3 PEtn_1 HexNAc_1$ anhydroKDO$_1$ |
| | 742.1 | 1465.2 | 1465.2 | $Hex_2 Hep_3 PEtn_1 HexNAc_1 KDO_1$ |

[a] Based on average atomic masses.
[b] Hex, HexNAc, Hep, KDO, PEtn and Fuc designate hexose, hexosamine, heptose, 3-keto-deoxy-D-manno-2-octulosonic acid, phosphoethanolamine and fucose, respectively.

Example 3

Characterization of O-Deacylated 26695 HP0826::Kan LPS by CE-MS

Figure 2:
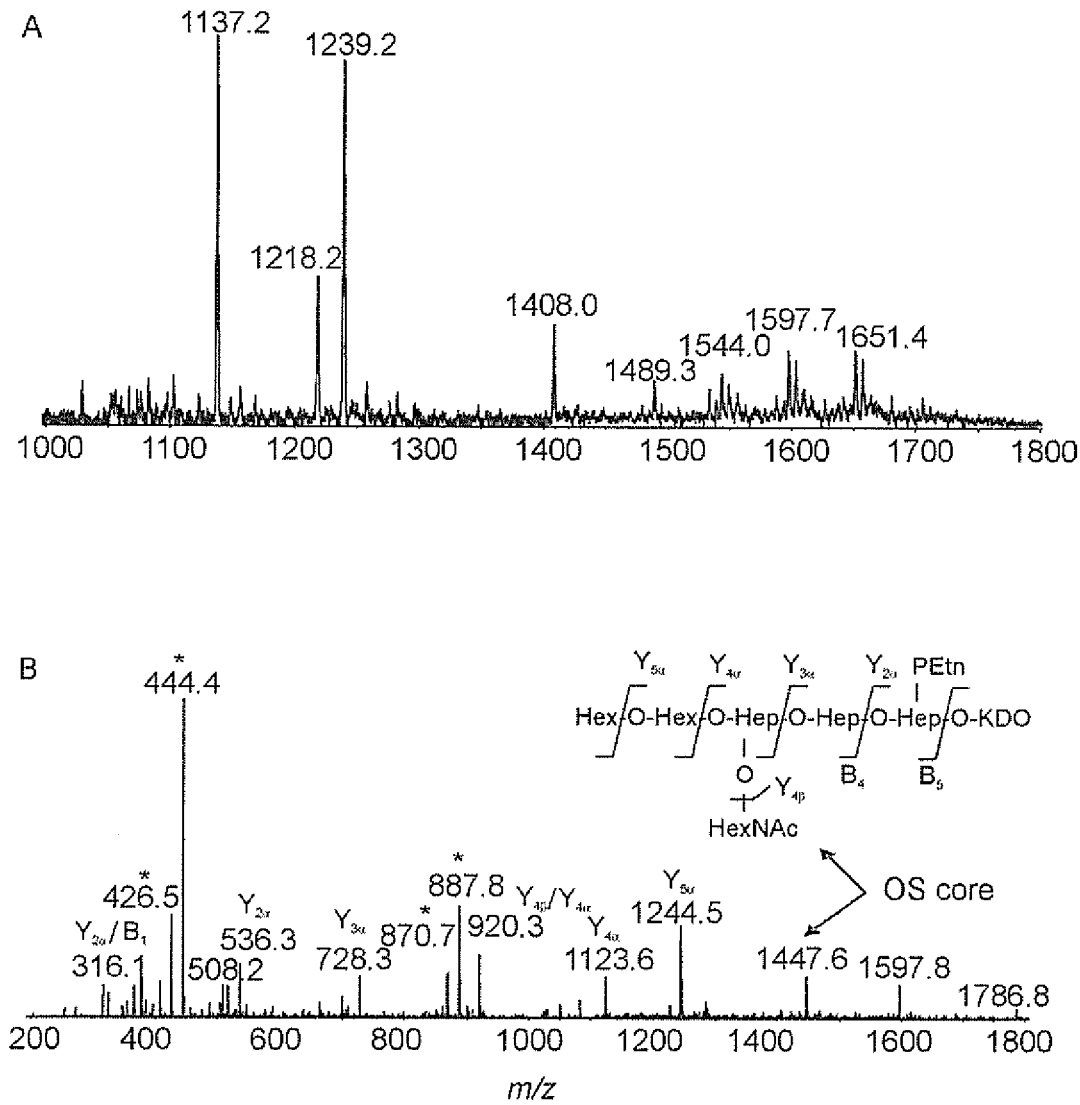
FIG. 2 shows a CE-MS analysis of LPS glycoforms of the O-deacylated LPS from *H. pylori* strain 26695 HP0826::Kan in the negative ion mode.

O-Deacylation of 26695 HP0826::Kan LPS (of Example 1) was carried out according to Hoist et al. (1991) with some modifications. Briefly, LPS (4 mg) was stirred in anhydrous hydrazine (0.2 ml) at 37° C. for 4 h. The reaction mixture was cooled, and cold acetone (2 ml) was slowly added to destroy excess hydrazine. After 30 min, precipitated O-deacylated LPS (LPS-OH) was collected by centrifugation (4° C., 9300×g 10 min.). The pellet was washed twice with cold acetone dissolved in water and lyophilized to give LPS-OH (3.5 mg).

and [HexAc, Fuc, Hep], respectively (Table 2), while triply charged ions at m/z 1597.7, m/z 1651.4 and m/z 1705.5 were consistent with the presence of glucan, the longest glucan chain corresponding to approximately twelve α1,6-linked residues (Table 2, FIG. 2). The MS/MS spectrum of m/z 1597.7 showed the presence of diagnostic ions at m/z 1447.6 and m/z 1244.5 consistent with the sequential loss of [Fuc, Hep] and [Fuc,Hep,HexNAc], respectively (FIG. 2) and, additionally, gave rise to a singly charged ion at m/z 1786.8 consistent with the core fragment $FucHex_2 HexNAcHep_4$ (PEtn)Kdo linked via a Kdo residue to O-deacylated lipid A (lipid A-OH), while ions at m/z 444.4 and m/z 887.8 corresponded to the lipid A-OH moiety consisting of a diglucosamine backbone substituted with two amide-linked 3-hydroxyoctadecanoic [C18:0(3-OH)] fatty acid chains (FIG. 2).

TABLE 2

Positive-ion CE-MS data and proposed composition of LPS glycoforms in O-deacylated LPS from *H. pylori* strain 26695 HP0826::Kan.

| Observed ion (m/z) | Molecular mass Observed | Calculated[a] | Proposed composition[b] |
|---|---|---|---|
| $[M + 2H]^{2+}$ | | | |
| 1137.2 | 2272.4 | 2272.1 | $Hex_2 Hep_3 PEtn_2 HexN_2$ (3-OH C18:0)$_2 KDO_1$ |
| 1239.2 | 2476.6 | 2475.3 | $Hex_2 Hep_3 HexAc_1 PEtn_2 HexN_2$ (3-OH C18:0)$_2 KDO_1$ |
| 1408 | 2814.4 | 2813.5 | $Fuc_1 Hex_2 Hep_4 HexNAc_1 PEtn_2 HexN_2$ (3-OH C18:0)$_2 KDO_1$ |

TABLE 2-continued

Positive-ion CE-MS data and proposed composition of LPS glycoforms in
O-deacylated LPS from *H. pylori* strain 26695 HP0826::Kan.

| Observed ion | Molecular mass | | |
|---|---|---|---|
| (m/z) | Observed | Calculated[a] | Proposed composition[b] |

$[M + 3H]^{3+}$

| | | | |
|---|---|---|---|
| 1597.7 | 4790.1 | 4789.2 | $Fuc_1 Hex_{13} Hep_5 HexNAc_1 PEtn_2 HexN_2$ (3-OH C18:0)$_2$ KDO$_1$ |
| 1651.4 | 4951.2 | 4951.3 | $Fuc_1 Hex_{14} Hep_5 HexNAc_1 PEtn_2 HexN_2$ (3-OH C18:0)$_2$ KDO$_1$ |
| 1705.5 | 5113.5 | 5113.5 | $Fuc_1 Hex_{15} Hep_5 HexNAc_1 PEtn_2 HexN_2$ (3-OH C18:0)$_2$ KDO$_1$ |

[a]Based on the average atomic masses.
[b]Hex, HexN, Hep, KDO, PEtn and Fuc designate hexose, hexosamine, heptose, 3-keto-deoxy-D-manno-2-octulosonic acid, phosphoethanolamine and fucose, respectively.

Example 4

NMR Analysis of *H. pylori* Strain 26695 HP0826::Kan LPS

Degradation of the LPS from *H. pylori* strain 26695 HP0826::Kan (of Example 1) was initiated with complete deacylation with 4 M KOH in the presence of NaBH$_4$ for the instant reduction of lipid A GlcN, since alkaline hydrolysis of PEtN substituent leaves reducing end GlcN without aglycon (Hoist et al., 1991). Separation of the products by gel chromatography gave two fractions, eluted in the oligosaccharide region of the chromatogram. Further analysis showed that these fractions contained similar compounds, apparently differing by the length of a glucan chain. Lower molecular mass fraction contained compounds 1-3, identified by mass spectrometry, and both fractions contained compound 4 with different length of glucan portion (FIG. 3).

NMR spectra (DQCOSY, TOCSY, NOESY, $^1H$-$^{13}C$ HSQC and HMBC) were performed on a VARIAN™ 500 or 600 MHz spectrometer using standard software as described previously (Brisson et al., 2002). All NMR experiments were performed at 25° C. using acetone as an internal reference at δ 2.225 ppm for $^1H$ spectra and 31.45 ppm for $^{13}C$ spectra.

NMR spectra of both fractions corresponded to compound 4, although spectra could not be completely interpreted due to their complexity. The H-1 protons of terminal residues of α1,6-glucan and DD-heptan did not overlap with the rest of glucan and heptan H-1, thus allowing identification of the position of these homopolymers within the entire structure, as shown in FIG. 3. However, the linkage position of the reducing terminal Glc residue Z of the α1,6-glucan chain was not determined. It showed strong NOE correlation with an unidentified proton (later assigned to H-6 of Hep N). NMR data of the compound 4 clearly showed that α1,6-glucan was placed between DD-heptan and inner core, since the first Hep residue of the heptan moiety (X) was linked to O-3 of a non-reducing terminal Glc residue V belonging to α1,6-glucan. The non-reducing end of DD-heptan was substituted at O-3 with β-GlcN W. Compounds identical to smaller oligosaccharides 1-3 were previously found as main components of the *H. pylori* LPS of the α1,6-glucan-less mutant HP0159::Kan and NMR data for them were published (Altman et al., 2008). Selected NMR data for the compound 4 are shown in Table 3. It can be clearly seen that the previously proposed sequence of four contiguous heptose residues linked to Kdo was not present in any of the examined compounds (FIG. 3). The β-GlcN residue L was linked directly to O-2 of Hep G, and there was no GlcN connected to O-7 of Hep in any part of the LPS structure.

TABLE 3

$^1H$ and $^{13}C$-NMR assignments for compound 4.

| Unit | H/C 1 | H/C 2 | H/C 3 | H/C 4 | H/C 5 | H/C 6 | H/C 7 |
|---|---|---|---|---|---|---|---|
| Hep G | 5.19 | 4.35 | 3.95 | 3.83 | 3.85 | 4.24 | 3.78/4.14 |
| | 100.5 | 77.1 | 70.6 | 68.7 | 74.7 | 70.7 | 72.0 |
| GlcN L | 4.91 | 3.36 | 3.78 | 3.64 | 3.52 | 3.79/3.95 | |
| | 97.8 | 56.4 | 83.7 | 69.6 | 77.6 | 61.5 | |
| Fuc M | 5.05 | 4.05 | 4.02 | 4.01 | 4.28 | 1.21 | |
| | 103.0 | 69.5 | 77.7 | 72.5 | 69.0 | 16.3 | |
| Hep N | 5.15 | 4.05 | 3.91 | 3.84 | 3.84 | 4.08 | 3.90/3.90 |
| | 102.8 | 71.1 | 71.3 | 68.7 | 74.5 | 79.8 | 62.0 |
| Glc Z | 5.15 | 3.61 | 3.74 | 3.52 | 4.11 | 3.76/3.99 | |
| | 98.9 | 72.5 | 74.5 | 70.7 | 71.6 | 66.7 | |
| Hep P | 5.26 | 4.34 | 3.96 | 3.84 | 3.87 | 4.06 | 3.74/3.81 |
| | 100.8 | 77.1 | 70.7 | 68.7 | 74.6 | 72.8 | 63.0 |
| GlcN W | 4.86 | 3.17 | 3.68 | 3.52 | 3.52 | 3.78/3.93 | |
| | 98.2 | 56.3 | 73.1 | 70.8 | 77.6 | 61.5 | |

For further analysis of the LPS structure compounds 1-4 were deaminated. Briefly, the samples were dissolved in 10% AcOH and an excess of NaNO$_2$ was added; after 3 h, product was isolated by gel chromatography on SEPHADEX™ G-15 column. Some compounds were then reduced with NaBD$_4$ and desalted. The resulting products were compounds 5 and 6. NMR spectra of compound 5 (performed as described above) showed two isomers with phosphate at position 6 or 7 of the Hep E (due to phosphate migration under alkaline conditions). Again, three contiguous Hep residues were present, not four as would have been expected if the previously proposed structure were correct. Removal of the entire side chain by deamination procedure (described above) confirmed that GlcN L formed the connection between sugars of the OS 5 and the remainder of the molecule.

Compound 6 contained DD-heptan, α1,6-glucan and trisaccharide DDHep-Fuc-anh-Man-ol (N-M-L, anh-Man L deriving from GlcN L) at the reducing end. Spectra of this product were less crowded and it became possible to identify the attachment point of the α-1,6-glucan to O-6 of the DDHep N (from TOCSY between H-1 and H-6 of DDHep N). The structure was linear, as confirmed by methylation analysis, which showed no branched sugars; all expected products were identified in agreement with the proposed structure (Table 4).

The size of the DD-heptan domain could be estimated: compound 8 contained four mannose residues, derived from DD-heptose. Spectra of compound 8 were well resolved and integration of H-1 signals gave nearly equimolar ratio and showed the presence of four mannose residues. Thus, the intact DD-heptan domain in compound 6 consisted mostly of 5 DD-heptose units, one of which (terminal) was removed by periodate oxidation. This conclusion was confirmed by mass spectrometry. The structure of the major LPS glycoform produced by *H. pylori* strain 26695 HP0826::Kan is illustrated in FIG. 3.

TABLE 4

$^1$H- and $^{13}$C-NMR assignments for compound 6.

| Unit, compound | H/C 1 | H/C 2 | H/C 3 | H/C 4 | H/C 5 | H/C 6 | H/C 7 |
|---|---|---|---|---|---|---|---|
| anh-Man-ol L | 3.75 | 4.08 | 4.07 | 4.20 | 3.94 | 3.72/3.79 | |
|  | 62.1 | 82.6 | 84.4 | 76.6 | 83.8 | 62.0 | |
| Fuc M | 4.95 | 3.91 | 3.97 | 4.01 | 4.21 | 1.21 | |
|  | 99.8 | 68.7 | 77.7 | 72.6 | 68.3 | 16.3 | |
| Hep N | 5.11 | 4.05 | 3.96 | 3.83 | 3.85 | 4.08 | 3.89 |
|  | 103.3 | 71.0 | 72.5 | 68.8 | 75.0 | 79.8 | 62.0 |
| -6-Glc Z | 5.16 | 3.61 | 3.75 | 3.52 | 4.13 | 3.75/4.00 | |
|  | 98.9 | 72.5 | 74.5 | 70.7 | 71.6 | 66.7 | |
| -6-Glc Q | 4.99 | 3.59 | 3.73 | 3.52 | 3.91 | 3.75/4.00 | |
|  | 98.9 | 72.5 | 74.5 | 70.7 | 71.4 | 66.7 | |
| -3-Glc V | 4.98 | 3.63 | 3.86 | 3.58 | 3.73 | 3.76/3.84 | |
|  | 98.9 | 71.4 | 80.8 | 71.0 | 72.9 | 61.4 | |
| Hep X | 5.22 | 4.22 | 3.94 | 3.94 | 3.89 | 4.06 | 3.73/3.82 |
|  | 102.0 | 70.8 | 79.2 | 67.6 | 75.0 | 72.5 | 62.8 |
| Hep Y | 5.10-5.11 | 4.25 | 3.98 | 3.89 | 3.89 | 4.06 | 3.73/3.82 |
|  | 103.3 | 70.6 | 79.0 | 67.9 | 75.0 | 72.5 | 62.8 |
| Hep T | 5.11 | 4.25 | 3.98 | 3.89 | 3.89 | 4.06 | 3.73/3.82 |
|  | 103.3 | 70.6 | 79.0 | 67.9 | 75.0 | 72.5 | 62.8 |
| Hep P | 5.12 | 40.6 | 3.85 | 3.75 | 3.89 | 4.06 | 3.73/3.82 |
|  | 103.3 | 71.0 | 71.8 | 68.6 | 75.0 | 72.5 | 62.8 |

Further confirmation of the structure of DD-heptan-α-1,6-glucan region was obtained from the results of the periodate oxidation of compound 6. Periodate oxidation was performed with an excess of 0.1 M NaIO$_4$ for 24 h; ethyleneglycol was added and product isolated by gel chromatography on SEPHADEX™ G-15 column. It was reduced with NaBD$_4$, desalted, and hydrolyzed with 2% AcOH for 3 h at 100° C. Two main products, 7 and 8, were obtained and isolated by gel chromatography on SEPHADEX™ G-15 column.

The reduction of oxidized oligosaccharide with NaBD$_4$ allowed identification of the oxidized carbons in NMR spectra (inverted phase of CHDOH signals as compared with CH$_2$OH signals in APT-HSQC). The structure of compounds 7 and 8 was determined by NMR spectroscopy and methylation analysis. Formation of compound 7 proved that DDHep N was not substituted at position 3. Since methylation of compound 6 showed only terminal, 3- and 6-substituted DD-Hep, DD-Hep N was substituted at position 6, as it was proposed from NMR data of compound 6. Formation of compound 8 with glycerol (Gro) at the reducing end confirmed that Glc V in the OS 6 glycosylated next Glc residue at position 6, since there were no other components of the oligosaccharide 6 which could produce glycerol upon oxidation-reduction. It also clearly proved the attachment of the DD-heptan moiety to the non-reducing end of α-1,6-glucan at position 3 of terminal glucose.

Example 5

Preparation and Characterization of LPS-OH-TT, dLPS-BSA, dLPS-TT, and dLPS(PJ2)-TT Conjugates Kdo-linked conjugates of LPS-OH (see Example 3) and dLPS (see Example 2) to bovine serum albumin (BSA) and/or tetanus toxoid (TT) were prepared.

LPS-OH (4 mg, 0.8 µmol, based on an estimated average molecular mass of 4789 Da) or dLPS (4 mg, 1 µmol, based on an estimated average molecular mass of 3779 Da) was dissolved in 0.1 M 2-(N-morpholino)ethanesulfonic acid (MES; SIGMA-ALDRICH™, St. Louis, Mo.) buffer, pH 4.8, containing 0.1 M NaCl (0.4 mL); 1-ethyl-3-dimethylaminopropyl carbodiimide (EDC; 34.38 mg, 100:1 molar ratio; SIGMA-ALDRICH™) was added followed by 1,8-diamino-3,6-dioxaoctane (15 µL, 103 µmol; SIGMA-ALDRICH™), and the reaction was maintained at pH 4.8 for 4 h at 22° C. The solution was adjusted to pH 7.0 and dialyzed against distilled water or desalted using a MICROSEP™ centrifugal device, 1,000 Da cutoff (PALL LIFE SCIENCES™, Ann Arbor, Mich.) and lyophilized.

The conjugation procedure was carried out essentially as described for oligosaccharides by Fernandez-Santana et al. (1998). Briefly, the spacer-containing LPS-OH (2 mg, 0.4 µmol) or dLPS (2 mg, 0.5 µmol) was reacted with 3-maleimidopropionic acid N-hydroxysuccinimide ester (BMPS; 2 mg, 7.5 μmol; SIGMA-ALDRICH™) in dry DMSO for 24 h at 22° C. The solution was dialyzed against distilled water, and lyophilized.

For activation of BSA, 3,3'-dithiodipropionic acid di(N-hydroxysuccinimide ester) (DTSP; 0.63 mg, 1.6 μmol; SIGMA-ALDRICH™) in dry DMSO, was added, under $N_2$ atmosphere, to a solution of bovine serum albumin (BSA) (molecular mass 66,320 Da) (8 mg, 0.12 μmol) previously dissolved in 10 mM PBS buffer, pH 8.0, containing 6 mM EDTA (final concentration 4 mg/mL), and the mixture was stirred for 2 h at 22° C. This was followed by addition of dithiothreitol (DTT; 7.12 mg, 46 μmol; SIGMA-ALDRICH™), under $N_2$ atmosphere, and the mixture was stirred for 1 h at 4° C. The resulting solution was dialyzed against 10 mM PBS buffer, pH 7.2, containing 5 mM EDTA in a stirred ultrafiltration cell (MILLIPORE™, Billerica, Mass.), using $N_2$ as a pressure source, over a regenerated cellulose membrane, 30,000 Da cutoff (YM30, MILUPORE™) at 4° C. The protein and SH contents were determined by bicinchoninic acid protein assay kit (BCA; PIERCE™, Rockford, Ill.) and Ellman (1959) methods, respectively. A molar substitution of 20-22 SH groups was attained.

For the activation of tetanus toxoid (TT) (molecular mass, 150,000 Da), DTSP (0.316 mg, 0.8 μmol) in dry DMSO (25 μL) was added, under $N_2$ atmosphere, to a solution of TT (4 mg, 0.03 μmol) in 10 mM PBS buffer, pH 8.0, containing 6 mM EDTA (final concentration 4 mg/mL), and the reaction was allowed to proceed as described for BSA. This was followed by addition of dithiothreitol (DTT; 3.56 mg, 23 μmol; SIGMA-ALDRICH™), under $N_2$ atmosphere, and the mixture was stirred for 1 h at 4° C. Activated TT was transferred to a stirred ultrafiltration cell (MILLIPORE™) and dialyzed against 10 mM PBS buffer, pH 7.2, containing 5 mM EDTA over a regenerated cellulose membrane, 100,000 Da cutoff (YM100™, MILLIPORE™) at 4° C.

To a solution of BSA-$SH_{21-22}$ or TT-$SH_{21-22}$ in 10 mM PBS buffer, pH 7.2, containing 5 mM EDTA, a solution of maleimido-functionalized LPS-OH or dLPS derivative in 10 mM PBS buffer, pH 7.2, containing 5 mM EDTA (final concentration 4 mg/mL) (3:1 molar ratio) was added under $N_2$ atmosphere. The reaction was stirred for 24 h at 4° C. This was followed by addition of N-ethylmaleimide (1 mg; SIGMA-ALDRICH™). The reaction was allowed to proceed for 30 min at 22° C., and the resulting conjugate was dialyzed against 10 mM PBS buffer, pH 7.2, for 4 d at 4° C. and filter sterilized using 0.22 μm polyvinylidene fluoride (PVDF) membrane (MILLEX-GV™, MILLIPORE™, Cork, Ireland). Conjugates were analyzed for their carbohydrate and protein content using phenol sulfuric acid method for neutral sugars (Dubois et al., 1956) and BCA protein assay kit (PIERCE), respectively, with LPS-OH or dLPS and BSA as standards. The efficiency of conjugation was confirmed by high performance liquid chromatography (HPLC; AGILENT 1200 SERIES™, AGILENT TECHNOLOGIES™, Waldbronn, Germany) using SUPEROSE 12 10/300 GL™ column (AMERSHAM BIOSCIENCES, Uppsala, Sweden) equilibrated with 10 mM PBS buffer pH 7.2. The chromatography was carried out at room temperature and at a flow rate 0.5 mL/min. The elution was monitored at 210 nm and 280 nm with diode array detector (AGILENT TECHNOLOGIES™).

The presence of a spacer was confirmed by $^1$H-NMR spectroscopy by the appearance of a new proton resonance at 3.22 ppm, corresponding to $CH_2NH_2$ group. The amine group of the spacer molecule was further derivatized by reaction with 3-maleimidopropionic acid N-hydroxysuccinimide ester to yield maleimido-functionalized LPS-OH or dLPS, as confirmed by the presence of proton resonances at 2.55 ppm and 6.9 ppm, corresponding to $CH_2\alpha$ and $CH=CH$ groups of β-maleimidopropionate, respectively (FIG. 4). Derivatization of phosphoethanolamine of the inner core LD-Hep was kept to a minimum by using stoichiometric amounts of the reagent. The glycoconjugate was obtained through thiolation of a carrier protein and addition of the thiolated protein to the maleimido-functionalized LPS-OH or dLPS (FIG. 4). The efficiency of conjugation was monitored by HPLC. The resultant conjugate was analyzed for its carbohydrate and protein content.

The molar ratio of LPS-OH to TT in three conjugates ranged from 10:1 to 20:1, and the yield ranged from 13% to 22%, based on the carbohydrate content (Table 5). Conjugation of dLPS to BSA or TT yielded dLPS-BSA-2, dLPS-TT or dLPS(PJ2)-TT conjugates with significantly higher carbohydrate content (Table 5). Both LPS-OH-TT and dLPS-BSA or dLPS-TT conjugates reacted equally well with α1,6-glucan-specific mAbs by ELISA suggesting that the conformation of the glucan epitope was unchanged.

TABLE 5

Composition and yield of conjugates used in this study.

| Conjugate | Amt (μg/mL) of CHO[1] | Amt (μg/mL) of protein[2] | Molar ratio of CHO[3] to protein | Yield (%) |
|---|---|---|---|---|
| LPS-OH-TT-1 | 120 | 260 | 15:1 | 22 |
| LPS-OH-TT-2 | 110 | 340 | 10:1 | 22 |
| LPS-OH-TT-3 | 80 | 120 | 20:1 | 13 |
| LPS-OH-TT-4 | 140 | 310 | 14:1 | 18 |
| dLPS-BSA-1 | 75 | 100 | 13:1 | 18 |
| dLPS-BSA-2 | 850 | 1200 | 13:1 | 29 |
| dLPS-TT | 490 | 960 | 20:1 | 16 |
| dLPS(PJ2)-TT | 390 | 760 | 24:1 | 32 |

[1]Amount of carbohydrate (CHO) was determined according to Dubois et al. (1956); LPS-OH or dLPS was used as a standard.
[2]Amount of protein was determined by BCA test; BSA was used as a standard.
[3]Molar ratio of CHO to protein was determined using average molecular mass values based on the average length of glucan chain: 4789 Da for LPS-OH and 3779 Da for dLPS (n = 10). For dLPS(PJ2) average molecular mass value was 3261 Da based on the average length of glucan chain (n = 8) (Altman et al., 2003).

Example 6

Immunogenicity of LPS-OH-TT, dLPS-BSA, dLPS-TT Conjugates and dLPS(PJ2)-TT Conjugates in Mice and Rabbits The immunogenicity of the conjugates (LPS-OH-TT, dLPS-BSA, dLPS-TT, and dLPS(PJ2)-TT) of Example 5 was tested in mice and rabbits.

Five 6-8 week old female BALB/c mice were immunised intraperitoneally with appropriate conjugates. Each mouse received 2 μg or 10 μg of carbohydrate in 0.2 mL Ribi adjuvant per injection. The mice were boosted on day 21 and 42 and sera recovered after terminal heart puncture on day 51.

Three New Zealand white rabbits were immunised subcutaneously with appropriate conjugates. Each rabbit received 10 μg or 50 μg of carbohydrate in 0.5 mL Incomplete Freunds adjuvant. The rabbits were boosted on day 28 and 56 and sera recovered after exsanguination on day 65.

The level of anti-LPS antibody in serum was measured by ELISA in which purified LPS was used as a coating antigen (1 μg/well). After washing with PBS, the plates were blocked with 1% (w/v) bovine serum albumin (BSA) in PBS or Milk Diluent/blocking solution (MDB) (KPL™, Gaithersburg, Md.) for 1 h at 37° C. Diluted mouse or rabbit pre- and post-immune sera were added, and the plates were incubated for 2 h at 37° C. For inhibition ELISA, serial dilutions of inhibiting 26695 HP0479::Kan LPS or 26695 HP0826::Kan LPS were mixed with previously determined dilution of rabbit sera that gave $OD_{450}$=0.6-0.8. This mixture was incubated for 15 min at 22° C. and then transferred to the original microtiter plate blocked with adsorbed LPS antigen, where it was incubated for another 2 h at 37° C. After this step, the indirect ELISA procedure was followed. Briefly, the plates were washed with PBS and the second antibody, a goat anti-mouse IgG+IgM horseradish peroxidase conjugate (CALTAG™, So. San Francisco, Calif.) was added for 1 h at room temperature. After a final washing step, 3,3',5,5'-tetramethylbenzidene (TMB) (KPL™, Gaithersburg, Md.) substrate was added and the reaction was stopped with 1 M phosphoric acid. The absorbance was determined at 450 nm using a microtiter plate reader (DYNATECH™, Chantilly, Va.).

The percentage inhibition was calculated using the following formula:

% inhibition=100×[(OD with inhibitor−OD without inhibitor)/OD without inhibitor]

inhibition versus log concentration curves were plotted for each inhibitor, and the concentrations required for the half maximal inhibitory concentration ($IC_{50}$) were determined from extrapolation curves.

All conjugates elicited an IgG response against LPS from the homologous (26695 HP0826::Kan) and corresponding wild-type (26695) strains in both rabbits and mice after three injections (Tables 6 to 9) although the response was generally weaker in LPS-OH-TT immunized mice and rabbits than in animals immunized with either dLPS-BSA, dLPS-TT or dLPS(PJ2)-TT. Control rabbits immunized with a mixture of either LPS-OH, dLPS or dLPS(PJ2) and a protein carrier (with an adjuvant) showed no or low level specific response to LPS from the homologous strain (26695 HP0826::Kan mutant) or corresponding wild-type 26695 strain of *H. pylori* after three immunizations.

TABLE 6

Murine and rabbit antibody responses to *H. pylori* 26695 HP0826::Kan LPS and 26695 LPS elicited by LPS-OH-TT conjugates.

| Immunogen | Immune serum | Serum endpoint IgG titre 1: 26695 LPS | 26695 HP0826::Kan LPS |
|---|---|---|---|
| LPS-OH-TT-1[a] | mice | | |
| | 1 | 1,597 | 16,853 |
| | 2 | 2,775 | 45,709 |
| | 3 | 2,436 | 13,594 |
| | 4 | 1,479 | 22,216 |
| | 5 | 5,495 | 8,940 |
| LPS-OH-TT-2[b] | rabbits | | |
| | 1 | 9,332 | 9,623,500 |
| | 2 | 4,641 | 3,715,400 |
| LPS-OH-TT-3[b] | rabbits | | |
| | 1 | 19,953 | 877,600 |
| | 2 | 22,903 | 245,470 |
| LPS-OH-TT-4[c] | rabbits | | |
| | 1 | 5,248 | 512,860 |
| | 2 | 1,765 | 813,760 |
| | 3 | 794 | 257,760 |
| LPS-OH, TT, IFA | 1 | 363 | 5,208 |
| | 2 | 871 | 430 |
| control | 1 | 45 | 85 |
| | 2 | 28 | 191 |

[a]Each mouse received 10 μg of carbohydrate per injection.
[b]Each rabbit received 50 μg of carbohydrate per injection.
[c]Each rabbit received 10 μg of carbohydrate per injection.

TABLE 7

Murine and rabbit antibody responses to *H. pylori* 26695 HP0826::Kan LPS and 26695 LPS elicited by dLPS-BSA conjugates.

| Immunogen | Immune serum | Serum endpoint IgG titre 1: 26695 LPS | 26695 HP0826::Kan LPS |
|---|---|---|---|
| | Balb/c mice | | |
| dLPS-BSA-1[a] | 1 | 27,968 | 87,096 |
| | 2 | 55,804 | 94,044 |
| | 3 | 8,844 | 78,223 |
| | 4 | 54,954 | 363,080 |
| dLPS-BSA-2[b] | 1 | 7,470 | 35,210 |
| | 2 | 1,445 | 2,797 |
| | 3 | 5,168 | 13,804 |
| | 4 | 9,848 | 59,338 |
| | 5 | 8,577 | 24,359 |
| | rabbits | | |
| dLPS-BSA-2[c] | 1 | 65,063 | 162,180 |
| | 2 | 30,667 | 28,184 |
| | 3 | 8,710 | 93,325 |
| dLPS, BSA, IFA | 1 | 103 | 126 |
| | 2 | 1,097 | 464 |
| control[d] | 1 | 92 | 238 |
| | 2 | 245 | 161 |

[a]Each mouse received 10 μg of carbohydrate per injection.
[b]Each mouse received 2 μg of carbohydrate per injection
[c]Each rabbit received 10 μg of carbohydrate per injection.
[d]Adjuvant (IFA) only.

TABLE 8

Murine and rabbit antibody responses to *H. pylori* 26695 HP0826::Kan LPS and 26695 LPS elicited by dLPS-TT conjugate.

| Immunogen | Immune serum | Serum endpoint IgG titre 1: 26695 LPS | 26695 HP0826::Kan LPS |
|---|---|---|---|
| | mice Balb/c | | |
| dLPS-TT[a] | 1 | 48,603 | 187,640 |
| | 2 | 8,848 | 64,072 |
| | 3 | 10,798 | 56,667 |
| | 4 | 8,577 | 80,662 |
| | 5 | 35,755 | 103,120 |
| | mice CD-1 | | |
| dLPS-TT[a] | 1 | 5,575 | 6,166 |
| | 2 | 147,910 | 281,840 |
| | 3 | 54,954 | 94,044 |
| | 4 | 111,340 | 486,030 |
| | 5 | 114,820 | 95,499 |
| | rabbits | | |
| dLPS-TT[b] | 1 | 64,565 | 857,700 |
| | 2 | 83,176 | 82,540 |
| | 3 | 1,148,200 | 207,330,000 |
| dLPS, TT, IFA | 1 | 13 | 27 |
| | 2 | 0 | 0 |
| control[c] | 1 | 0 | 0 |
| | 2 | 0 | 0 |

[a]Each mouse received 2 μg of carbohydrate per injection.
[b]Each rabbit received 10 μg of carbohydrate per injection.
[c]Adjuvant (IFA) only.

TABLE 9

Murine and rabbit antibody responses to *H. pylori* 26695 HP0826::Kan LPS and 26695 LPS elicited by dLPS(PJ2)-TT conjugate.

| Immunogen | Immune serum | Serum endpoint IgG titre 1: 26695 LPS | 26695 HP0826::Kan LPS |
|---|---|---|---|
| | mice Balb/c | | |
| dLPS(PJ2)-TT[a] | 1 | 912 | 2,651 |
| | 2 | 851 | 3,090 |
| | 3 | 864 | 6,026 |
| | 4 | 977 | 6,407 |
| | 5 | 926 | 6,119 |
| | rabbits | | |
| dLPS(PJ2)-TT[b] | 1 | 3,772,800 | 27,542,000 |
| | 2 | 186,210 | 4,677,400 |
| | 3 | 44,668,060 | 55,378,000 |
| dLPS(PJ2), TT, IFA | 1 | 182 | 626 |
| | 2 | 81 | 347 |
| control[c] | 1 | 0 | 0 |
| | 2 | 0 | 0 |

[a]Each mouse received 2 μg of carbohydrate per injection.
[b]Each rabbit received 10 μg of carbohydrate per injection.
[c]Adjuvant (IFA) only.

Cross-reactivity studies were performed with the post-immune sera of rabbits immunized with either LPS-OH-TT-2, LPS-OH-TT-3, LPS-OH-TT-4, dLPS-BSA-2, dLPS-TT, or dLPS(PJ2) against LPS from *H. pylori* strains representative of various LPS glycotypes (Monteiro, 2001) and selected mutant strains. Results are shown in Tables 10, 11 and 12.

TABLE 10

Rabbit antibody responses to purified *H. pylori* LPS elicited by LPS-OH-TT and dLPS-BSA conjugates[c].

| LPS | immune serum IgG response OD$_{450\,nm}$ | | | |
|---|---|---|---|---|
| | LPS-OH-TT-2 | LPS-OH-TT-3 | LPS-OH-TT-4 | dLPS-BSA-2 |
| 26695 | 1.103[a] (0.482)[b] | 1.241[a] (0.833)[b] | 0.562[a] (0.050)[b] | 1.341[a] (0.751)[b] |
| 26695 HP0826::Kan | 1.572 (1.430) | 1.521 (1.523) | 1.469 (0.529) | 1.553 (1.140) |
| O:3 | 0.810 (0.258) | 1.113 (0.685) | 0.626 (0.041) | 1.244 (0.634) |
| O:3 HP0826::Kan | 1.569 (1.386) | 1.541 (1.689) | 1.473 (0.492) | 1.568 (1.158) |
| PJ1 | 0.755 (0.145) | 1.168 (0.543) | 0.471 (0.046) | 1.344 (0.759) |
| PJ2 | 1.335 (0.721) | 1.465 (1.188) | 1.098 (0.219) | 1.509 (1.100) |
| SS1 | 0.534 (0.096) | 0.570 (0.101) | 0.403 (0.049) | 1.103 (0.457) |
| SS1 HP0826::Kan | 0.713 (0.121) | 0.695 (0.177) | 0.442 (0.032) | 1.259 (0.539) |

[a]Post-immune serum titre 1:100
[b]Post-immune serum titre 1:1,000
[c]OD$_{450}$ ± 10%

TABLE 11

Rabbit antibody responses[a] to purified *H. pylori* LPS elicited by dLPS-TT conjugate[b].

| LPS | Immune serum IgG response OD$_{450\,nm}$ | | |
|---|---|---|---|
| | rabbit 1 | rabbit 2 | rabbit 3 |
| 26695 | 0.611 | 0.446 | 0.95 |
| 26695 HP0826::Kan | 1.038 | 0.799 | 1.248 |
| 26695 HP0159::Kan | 0.504 | 0.115 | 0.963 |
| O:3 | 0.575 | 0.478 | 0.904 |
| O:3 HP0826::Kan | 0.98 | 0.73 | 1.235 |
| PJ1 | 0.668 | 0.572 | 1.002 |
| PJ2 | 0.846 | 0.836 | 1.059 |
| SS1 | 0.358 | 0.065 | 0.739 |
| SS1 HP0826::Kan | 0.359 | 0.078 | 0.911 |
| M6 | 0.342 | 0.147 | 0.752 |
| J99 | 0.316 | 0.105 | 0.730 |

[a]Post-immune serum titre 1:1,000.
[b]OD$_{450}$ ± 10%.

TABLE 12

Rabbit antibody responses[a] to purified *H. pylori* LPS elicited by dLPS(PJ2)-TT conjugate[b].

| LPS | Immune serum IgG response OD$_{450\,nm}$ | | |
|---|---|---|---|
| | rabbit 1 | rabbit 2 | rabbit 3 |
| 26695 | 0.611 | 0.265 | 0.645 |
| 26695 HP0826::Kan | 0.965 | 0.695 | 1.03 |
| 26695 HP0159::Kan | 0.895 | 0.721 | 0.896 |
| O:3 | 0.351 | 0.181 | 0.369 |
| O:3 HP0826::Kan | 0.76 | 0.55 | 0.868 |
| PJ1 | 0.682 | 0.375 | 0.721 |
| PJ2 | 0.897 | 0.764 | 1.067 |
| SS1 | 0.271 | 0.136 | 0.219 |
| SS1 HP0826::Kan | 0.427 | 0.225 | 0.405 |

[a]Post-immune serum titre 1:1,000.
[b]OD$_{450}$ ± 10%.

The reactivity of post-immune sera obtained from rabbits that were immunized with LPS-OH-TT-2, LPS-OH-TT-3, or LPS-OH-TT-4 was indicative of the requirement for the presence of α1,6-glucan since only weak cross-reactivity was obtained with SS1 and SS1 HP0826::Kan LPS, these being representative of *H. pylori* strains unable to add 1,6-glucan (Logan et al., 2005) (Table 10). Surprisingly, sera obtained from rabbits that were immunized with dLPS-TT also recognized core LPS epitopes that did not contain any α1,6-glucan, namely LPS from strains SS1, SS1 HP0826::Kan, M6 and J99 (Table 11), showing a broader core recognition and inferring that dLPS-TT conjugate was more immunogenic, possitency H. pylori strain 26695 cells were used as a positive control. Assays did not vary by more than 10%.

Sera derived from rabbits that were immunized with dLPS-TT conjugate showed the strongest cross-reactivity to all strains tested (Table 13) using whole cell indirect ELISA.

TABLE 13

Cross-reactivity of rabbit post-immune sera[a] in the whole-cell indirect ELISA[b] against clinical isolates of H. pylori.

| Immunogen | rabbits | Strains | | | | | | | | | |
| --- | --- | --- | --- | --- | --- | --- | --- | --- | --- | --- | --- |
| | | 002CL | 026CL | 027CL | 048CL | 058CL | 101CL | 113CL | 153CL | 217CL | 240CL |
| LPS-OH-TT-2 | 1 | 0.215 | 0.298 | 0.637 | 0.141 | 0.567 | 0.386 | 0.629 | 0.591 | 0.312 | 0.771 |
| | 2 | 0.132 | 0.104 | 0.484 | 0.072 | 0.491 | 0.248 | 0.481 | 0.475 | 0.245 | 0.635 |
| LPS-OH-TT-3 | 1 | 0.311 | 0.333 | 0.644 | 0.121 | 0.606 | 0.484 | 0.678 | 0.587 | 0.347 | 0.803 |
| | 2 | 0.248 | 0.229 | 0.575 | 0.118 | 0.308 | 0.242 | 0.256 | 0.211 | 0.177 | 0.368 |
| LPS-OH-TT-4 | 1 | 0.213 | 0.359 | 0.492 | 0.105 | 0.393 | 0.431 | 0.673 | 0.639 | 0.246 | 0.717 |
| | 2 | 0.125 | 0.231 | 0.305 | 0.103 | 0.253 | 0.295 | 0.225 | 0.246 | 0.169 | 0.266 |
| | 3 | 0.138 | 0.277 | 0.386 | 0.07 | 0.288 | 0.352 | 0.378 | 0.348 | 0.153 | 0.384 |
| dLPS-BSA-2 | 1 | 0.995 | 0.694 | 0.916 | 0.283 | 0.738 | 1.126 | 0.995 | 1.14 | 0.448 | 1.02 |
| | 2 | 0.712 | 0.544 | 0.337 | 0.299 | 0.372 | 0.821 | 0.522 | 0.655 | 0.271 | 0.694 |
| | 3 | 0.773 | 0.664 | 0.351 | 0.502 | 0.475 | 0.884 | 0.788 | 0.947 | 0.443 | 0.791 |
| dLPS-TT | 1 | 0.835 | 1.167 | 0.621 | 0.945 | 0.876 | 1.471 | 1.300 | 1.277 | 1.146 | 1.243 |
| | 2 | 0.737 | 0.429 | 0.582 | 0.143 | 0.527 | 1.225 | 1.135 | 0.634 | 0.515 | 1.025 |
| | 3 | 0.838 | 1.168 | 0.652 | 0.999 | 0.823 | 1.500 | 1.361 | 1.254 | 1.118 | 1.157 |

[a]Post-immune serum titre 1:100.
[b]OD$_{450}$ ≥ 0.2 ± 10%.

bly due to the presence of TT carrier protein (Table 11). Alternatively, as the conjugates were prepared from a mixture of 3 glycoforms, the immune response may have been generated to other minor LPS components; this could explain the observed cross-reactions.

To probe the binding specificity of rabbit sera elicited by dLPS-TT conjugate, inhibition ELISA was conducted with purified 26695 HP0479::Kan LPS consisting of two glycoforms (approx. ratio 1:1), a linear backbone oligosaccharide structure and a linear backbone oligosaccharide capped with [GlcNAc, Fuc](Hiratsuka et al., 2005), and 26695 HP0826::Kan LPS. Binding of rabbit sera to glucan-negative LPS from strains SS1, SS1 HP0826::Kan HP0159::Kan and SS1 HP0479::Kan (FIG. 6) was significantly inhibited when 26695 HP0479::Kan LPS was used as an inhibitor, while 26695 HP0826::Kan LPS was the most effective inhibitor when 26695 LPS was used as a coating antigen (FIG. 6).

The ability of rabbit post-immune sera to recognize heterologous typeable and non-typeable strains was also validated in the whole cell indirect ELISA (WCE) against selected clinical isolates of H. pylori representatives of both typeable and non-typeable strains of H. pylori. The whole-cell indirect ELISA (WCE) was performed as previously described (Altman et at, 2008). Briefly, the wells of a microtiter plate were coated with 100 μL of a bacterial suspension, 10$^8$ cells/mL, overnight, at 4° C. The wells were then fixed with methanol and blocked with 200 μL of Milk Diluent/Blocking solution (MDB) (KPL™, Gaithersburg, Md.) for 2 h at 37° C. Subsequently, the wells were incubated for 2 h at 37° C. with 100 μL of 1C4F9 ascites diluted 1:500 in MDB, followed by anti-mouse IgG+IgM horseradish peroxidase (CALTAG™) diluted 1:1,000 in MDB for 1 h at room temperature. The substrate TMB was added as described for indirect ELISA. The non-specific background values were determined as OD$_{450}$ of the negative control wells containing bacterial cells, secondary antibody conjugate and substrate. These OD$_{450}$ values were ≤0.2. The optical density values of OD$_{450}$<0.2 were classified as negative and OD$_{450}$ values≥0.2 were classified as positive reactions. To ensure plate to plate consis- Example 7

Bactericidal Activity of Rabbit Antisera

A bactericidal assay using pre- or post-vaccinated rabbit sera (Example 6) was performed.

Plate-grown H. pylori cells were harvested and washed with 5 mL of PBS per plate. Following centrifugation, pellets were suspended in 25 mL of PBS. The final bacterial suspension was diluted in Dulbecco's phosphate-buffered saline (DPBS) (INVITROGEN™, Grand Island, N.Y.) at 4×10$^6$ CFU/mL. The bactericidal assay was performed in a flat-bottomed microtiter plate (ICN). A ten-fold serial dilution of de-complemented pre- or post-immune sera (50 μL) was added to each well. Bacterial suspension (25 μL) was then added and pre-incubated for 15 min at 37° C. Baby rabbit complement (CEDARLANE LABORATORIES™, Hornby, ON) was diluted 1:50 and 25 μL was added to the appropriate wells. The plate was incubated for 45 min at 37° C. and then placed on ice. A 10 μL aliquot was plated in triplicate on Columbia blood agar, grown for 4 days, and then the plates were counted to measure the number of colony forming units (CFU). The control plate with bacteria and complement but without sera was used to calculate the percentage killing. The bactericidal activity was determined as the highest dilution of sera that caused 50% killing.

Pre-vaccination sera or sera obtained from rabbits immunized with a mixture of a protein carrier and either LPS-OH, dLPS, or dLPS(PJ2) (with an adjuvant) showed no or low levels of bactericidal activity against the homologous H. pylori 26695 HP0826::Kan or wild-type 26695 strains. The post-immune sera obtained from rabbits immunized with LPS-OH-TT-4, dLPS-BSA-2, dLPS-TT and dLPS(PJ2)-TT showed significant functional activity against both 26695 HP0826::Kan mutant and corresponding wild-type strains (Table 14) with postvaccination sera from rabbits immunized with dLPS-TT conjugate exhibiting the highest functional activity against wild-type strain 26695 (Table 14).

TABLE 14

Bactericidal activity against *H. pylori* strains 26695
HP0826::Kan and 26695 with rabbit antisera elicited by conjugates.

| Immunogen | Immune serum rabbits | Serum bactericidal titre (50% killing) against *H. pylori* 1: | |
|---|---|---|---|
| | | 26695 | 26695 0826::Kan |
| LPS-OH-TT-4[a] | 1 | 509 | 3,861 |
| | 2 | 374 | 5,934 |
| | 3 | 832 | 8,577 |
| control[b] | | 86 | 103 |
| dLPS-BSA-2[a] | 1 | 884 | 13,183 |
| | 2 | 398 | 5,580 |
| | 3 | 275 | 3,415 |
| control[b] | | 132 | 140 |
| dLPS-TT[a] | 1 | 1,131 | 4,365 |
| | 2 | 1,063 | 1,445 |
| | 3 | 4,105 | 4,936 |
| control[b] | | 158 | 124 |
| dLPS(PJ2)-TT[a] | 1 | 832 | 2,840 |
| | 2 | 1,848 | 2,671 |
| | 3 | 509 | 7,586 |
| control[b] | | 63 | 52 |

[a]Each rabbit received 10 μg of carbohydrate per injection.
[b]Corresponding rabbit preimmune serum.

Furthermore, bactericidal activity of the rabbit sera was also tested against selected clinical isolates of *H. pylori*, namely strains 002CL, 0153CL and 058CL (Altman et al., 2008). These isolates were selected as representatives of high, medium and low binders based on their OD$_{450}$ values in WCE assays with anti-α1,6-glucan mAbs: strain 002CL-OD$_{450}$1.361, high binder; strain 153CL-OD$_{40}$ 0.29, medium binder; and strain 058CL-OD$_{450}$ 0.162, low binder. It is important to emphasize that only the post-immune sera from rabbits immunized with either dLPS-TT or dLPS(PJ2)-TT conjugate showed functional activity with all three clinical isolates tested (Table 15).

TABLE 15

Bactericidal activity against clinical isolates of *H. pylori*
with rabbit antisera elicited by conjugates.

| Immunogen | Serum bactericidal titre (50% killing) against *H. pylori* 1: | | |
|---|---|---|---|
| | 002CL | 058CL | 153CL |
| LPS-OH-TT-4 | 1,131 | 407 | 0 |
| control[a] | 107 | 79 | 25 |
| dLPS-BSA-2 | 864 | 1,259 | 66 |
| control[a] | 93 | 75 | 53 |
| dLPS-TT | 509 | 1,445 | 311 |

TABLE 15-continued

Bactericidal activity against clinical isolates of *H. pylori*
with rabbit antisera elicited by conjugates.

| Immunogen | Serum bactericidal titre (50% killing) against *H. pylori* 1: | | |
|---|---|---|---|
| | 002CL | 058CL | 153CL |
| control[a] | 28 | 36 | 21 |
| dLPS(PJ2) | 374 | 1,738 | 215 |
| control[a] | 18 | 20 | 21 |

[a]Corresponding rabbit preimmune serum.

Example 8

Protection Studies by dLPS-TT Conjugate in Mice

The potential of dLPS-TT conjugate as a candidate vaccine was evaluated in outbred CD-1 mice.

Groups of 5 CD-1 mice were vaccinated four times intranasally at weekly intervals with 25 μg/mouse dLPS-TT conjugate, adjuvanted with 1 μg/mouse cholera toxin (CT; SIGMA™), 31.5 μg/mouse PJ2 cell-free sonicate adjuvanted with 1 μg/mouse cholera toxin (control), or saline (control). One week after the last immunization, serum, fecal and vaginal wash samples were collected and assayed for *H. pylori*-specific IgG and IgA. Serum IgG and serum, fecal and vaginal IgA antibody levels were determined by standard ELISA. Plates were coated with 1 μg/well *H. pylori* strain 26695 HP0826::Kan LPS as described herein. Serum samples were diluted 1:100 for IgG and 1:50 for IgA assay. Fecal samples were diluted 1:2 and vaginal samples were diluted 1:20. *H. pylori*-specific antibody levels were determined and the data was analyzed by Mann-Whitney analysis, using GRAPH-PAD™ software version 5.0.

Five weeks after the first immunization, mice were orally gavaged three times every other day with ~10$^8$ cfu *H. pylori* strain PJ2 (Altman et al., 2003). Four weeks later, mice were killed and viable bacteria from their stomachs were enumerated and the data were analyzed by Mann Whitney test, using GRAPHPAD™ software version 5.0.

Figure 7:
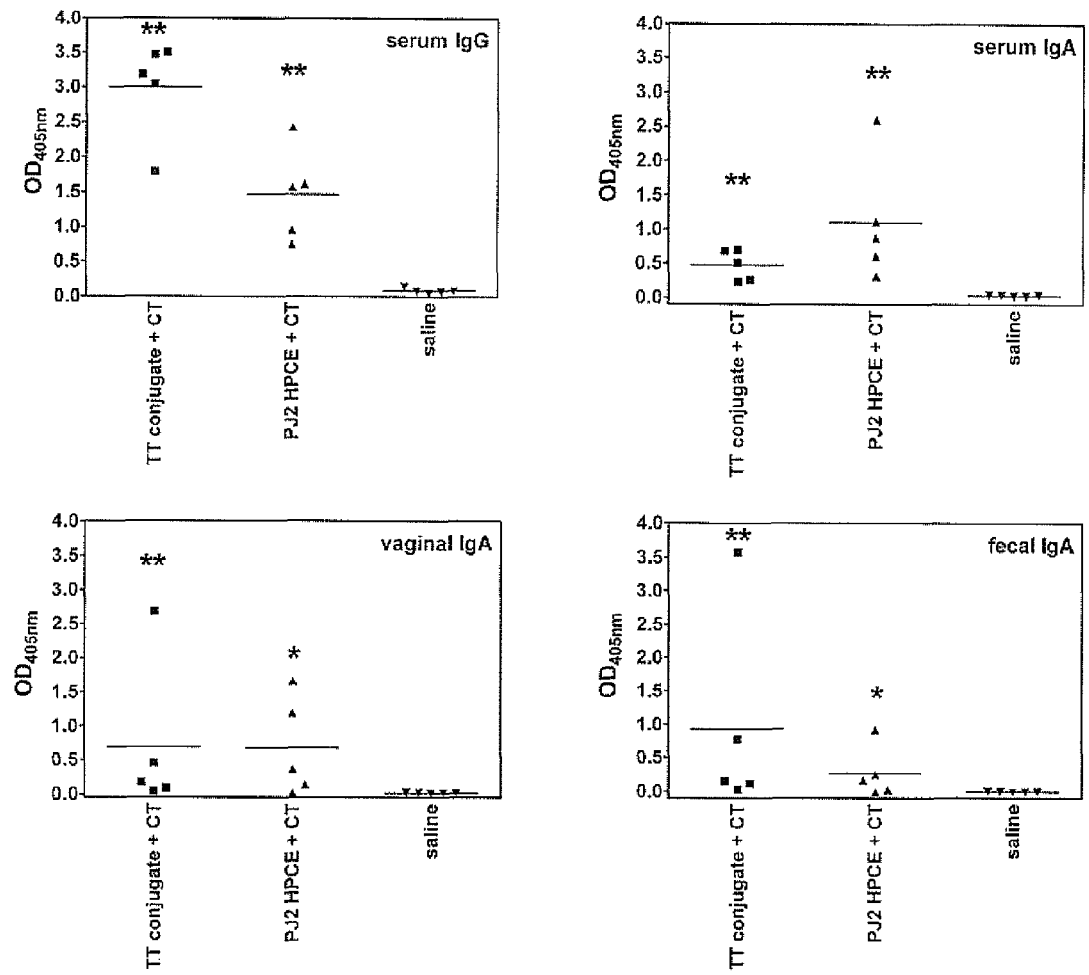
FIG. 7 shows graphs depicting the *H. pylori*-specific antibody responses in CD-1 mice. Mice were vaccinated four times at weekly intervals with 25 μg/mouse dLPS-TT conjugate adjuvanted with 1 μg/mouse cholera toxin (filled bars), PJ2 cell-free sonicate adjuvanted with 1 μg/mouse cholera toxin (hatched bars) or saline (open bars). Four weeks after the first immunization, serum, fecal and vaginal wash samples were collected and assays for *H. pylori*-specific IgG and IgA. Individual mice are plotted on the graphs with the horizontal bar indicating the group mean (n=5/group). * p<0.05, ** p<0.01 by one-tailed Mann Whitney test.

Intranasal immunization with dLPS-TT conjugate plus CT elicited a very strong *H. pylori* 26695 HP0826::Kan LPS-specific IgG response as measured by ELISA and moderate *H. pylori* 26695 HP0826::Kan LPS-specific serum IgA was also detected (Tables 16 and 17, FIG. 7). In addition, *H. pylori* 26695 HP0826::Kan LPS-specific IgA responses in vaginal or fecal samples were also detected (p<0.01) (Table 17, FIG. 7).

TABLE 16

*H. pylori* LPS-specific serum IgG levels measured by ELISA against 26695
HP0826::Kan LPS. Sera were collected at one week after the last immunization and prior
to bacterial challenge with *H. pylori* strain PJ2.

| | OD$_{405}$ (Mean ± SEM) serum IgG | | |
|---|---|---|---|
| Time point | dLPS-TT + CT | PJ2 sonicate + CT | Saline |
| Prechallenge | 3.004 ± 0.315 | 1.467 ± 0.295 | 0.089 ± 0.017 |

TABLE 17

H. pylori LPS-specific serum, fecal and vaginal IgA levels measured by ELISA against 26695 HP0826::Kan LPS. Samples were collected at one week after the last immunization and prior to bacterial challenge with H. pylori strain PJ2.

| Sample | $OD_{405}$ (Mean ± SEM) IgA | | |
|---|---|---|---|
| | dLPS-TT + CT | PJ2 sonicate + CT | Saline |
| Serum | 0.473 ± 0.100 | 1.099 ± 0.397 | 0.036 ± 0.004 |
| Feces | 0.689 ± 0.505 | 0.674 ± 0.321 | 0.017 ± 0.003 |
| Vaginal wash | 0.927 ± 0.674 | 0.269 ± 0.168 | −0.008 ± 0.002 |

Figure 8:
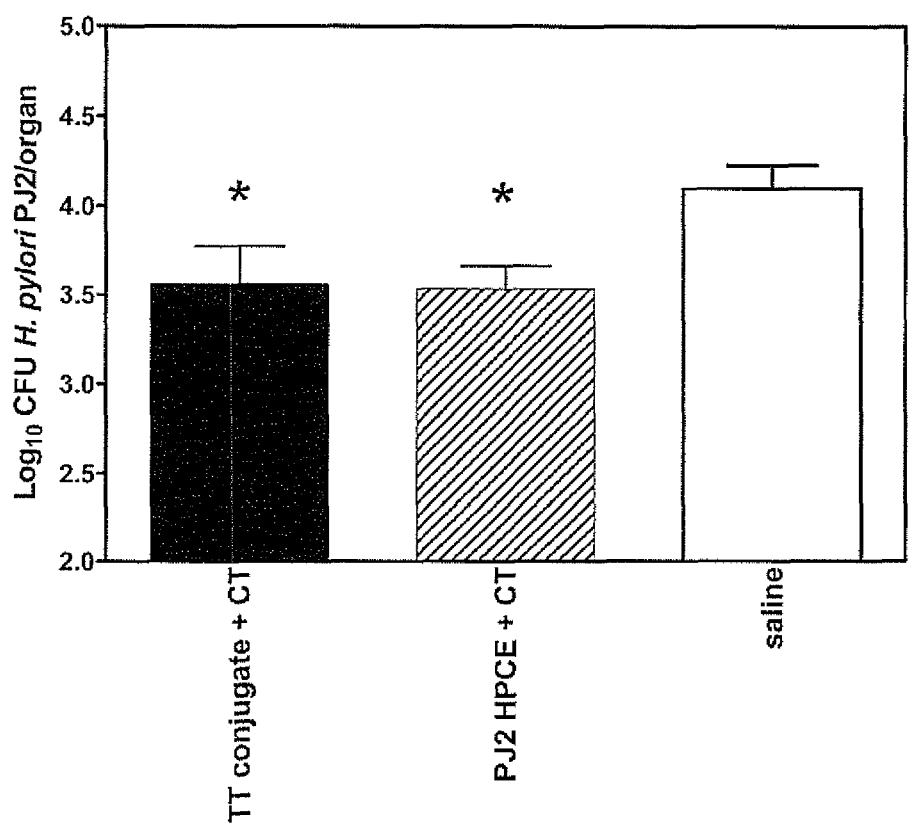
FIG. 8 is a bar graph depicting the *H. pylori* burdens in the stomachs of CD-1 mice. Mice were vaccinated four times at weekly intervals with 25 μg/mouse dLPS-TT conjugate adjuvanted with 1 μg/mouse cholera toxin (filled bars), PJ2 cell-free sonicate adjuvanted with 1 μg/mouse cholera toxin (hatched bars) or saline (open bars). Five weeks after the first immunization, mice were orally gavaged three times every other day with ~$10^8$ cfu *H. pylori*, PJ2 strain. Four weeks later, mice were killed and viable bacteria from their stomachs were enumerated. Bars represent groups of 4-5 mice±SEM.* $p<0.05$, one-tailed Mann-Whitney test.

All groups of mice were subsequently inoculated orogastrically with non-typeable H. pylori mouse-colonizing strain PJ2 previously shown to contain a long α1,6-glucan (Altman et al., 2003). Protection is defined as statistically significant decrease in bacterial load in vaccinated groups compared to control groups. The colonization data for groups of mice immunized intranasally with dLPS-TT conjugate plus CT was statistically significant (p<0.05) (FIG. 8). Moreover, these data suggest that H. pylori 26695 HP0826::Kan LPS-specific serum IgA responses alone may not be sufficient for protection against bacterial challenge and that LPS-specific serum IgG responses may also contribute to increased protection.

Example 9

Preparation and Characterization of Dextran-BSA Conjugate and Immunogenicity and Functional Activity Studies Dextran-BSA conjugate was prepared by dissolving 10 mg Dextran T5 (MW 5 KDa, PHARMACOSMOS A/T™, Holbaek, Denmark) in 250 µL of 0.2 M borate buffer, pH 9.0; this was added to a solution (250 µL) containing 1,8-diamino-3,6-dioxaoctane (25 µL) and sodium cyanoborohydride (10 mg) in 0.2 M borate buffer, pH 9.0 (as described by Roy et al., 1984). The reaction was carried out for 5 days at 55° C. The reaction product was purified as described above for preparation of LPS-based conjugates.

This reaction results in the introduction of a spacer. The amine group of the spacer molecule was further derivatized by reaction with 3-maleimidopropionic acid N-hydroxysuccinimide ester as described for LPS-based conjugates (see Example 5). The glycoconjugate was obtained through thiolation of a carrier protein and addition of the thiolated protein to the maleimido-functionalized Dextran T5. The molar ratio of Dextran to BSA in the conjugate was 20:1, and the yield was 32%, based on the carbohydrate content.

Cross-reactivity studies were performed with post-immune sera of rabbits immunized with Dextran-BSA against LPS from H. pylori strains representative of various LPS glycotypes and selected mutant strains (Table 18).

TABLE 18

Rabbit[a] antibody responses[b] to purified H. pylori LPS elicited by Dextran-BSA conjugate[c].

| | Immune serum IgG response $OD_{450\,nm}$ | |
|---|---|---|
| LPS | rabbit 1 | rabbit 2 |
| 26695 | 0.154 | 0.165 |
| 26695 HP0826::Kan | 0.440 | 0.348 |

TABLE 18-continued

Rabbit[a] antibody responses[b] to purified H. pylori LPS elicited by Dextran-BSA conjugate[c].

| | Immune serum IgG response $OD_{450\,nm}$ | |
|---|---|---|
| LPS | rabbit 1 | rabbit 2 |
| 26695 HP0159::Kan | 0.018 | 0.002 |
| O:3 | 0.109 | 0.074 |
| O:3 HP0826::Kan | 0.387 | 0.357 |
| PJ1 | 0.199 | 0.193 |
| PJ2 | 0.685 | 0.601 |
| SS1 | 0.06 | 0.001 |
| SS1 HP0826::Kan | 0.021 | 0.021 |

[a]Each rabbit received 10 µg of carbohydrate per injection.
[b]Post-immune serum titre 1:100.
[c]$OD_{450}$ ± 10%.

The reactivity of post-immune sera obtained from rabbits that were immunized with Dextran-BSA was indicative of the requirement for the presence of α1,6-glucan since no cross-reactivity was obtained with glucan-negative strains SS1 and SS1 HP0826::Kan.

The post-immune sera obtained from rabbits immunized with Dextran-BSA showed functional activity against both 26695 HP0826::Kan mutant and corresponding wild-type strain (Table 19).

TABLE 19

Bactericidal activity against H. pylori strains 26695 HP0826::Kan and 26695 with rabbit antisera elicited by Dextran-BSA conjugate.

| Immunogen | Immune serum rabbits | Serum bactericidal titre (50% killing) against H. pylori 1: | |
|---|---|---|---|
| | | 26695 | 26695 HP0826::Kan |
| Dextran-BSA[a] | 1 | 259 | 203 |
| control[b] | 2 | 374 | 149 |
| | | 15 | 13 |

[a]Each rabbit received 10 µg of carbohydrate per injection.
[b]Corresponding rabbit preimmune serum.

The ability of rabbit post-immune sera to recognize heterotogous typeable and non-typeable strains and induce bactericidal antibodies indicates the possibility that a conjugate consisting of Dextran, a polymer containing a linear backbone of α1,6-linked glucose repeating units, or a conjugate comprising optimized linear oligosaccharide/s consisting of consecutive α1,6-linked glucose residues, and a suitable protein carrier could be sufficient to confer protection against H. pylori infection.

Example 10

Specificity Studies of Anti-Glucan mAbs

Monoclonal antibodies specific to *H. pylori* strain O:3 HP0826::Kan were produced and their specificities studied.

Hybridomas were produced as previously described (Altman et al., 2005). Six BALB/c mice (Charles River Laboratories, St Constant, QC) were injected intraperitoneally (i.p.) with $10^8$ cells (200 µL) formalin-fixed cells of *H. pylori* strain O:3 HP0826::Kan 5 times over 82 days to achieve significant titer. A final intravenous (i.v.) injection was given and was followed 3 days later by fusion. The spleen cells of two mice were fused with an Sp2/O plasmacytoma cell line according to Kohler and Milstein (1975). Initial fusion supernatants from 368 wells were screened by indirect enzyme-linked immunosorbent assay (ELISA).

For hybridoma screening by ELISA, microtiter plates (ICN™, Costa Mesa, Calif.) were coated with 10 µg/mL of corresponding *H. pylori* O:3 HP0826::Kan LPS in 50 mM carbonate buffer, pH 9.8, for 3 h at 37° C. After washing with PBS, the plates were blocked with 5% (w/v) bovine serum albumin (BSA) in PBS. Spent supernatants were added, and the plates were incubated for 3 h at room temperature. The plates were washed with PBS and the second antibody, a goat anti-mouse IgG+IgM horseradish peroxidase conjugate (CALTAG™, So. San Francisco, Calif.) was added for 1 h at room temperature. After a final washing step, 3,3',5,5'-tetramethylbenzidene (TMB) (KPL™, Gaithersburg, Md.) substrate was added, and the reaction was stopped with 1 M phosphoric acid. The absorbance was determined at 450 nm using a microtiter plate reader (DYNATECH™, Chantilly, Va.). After this step, the indirect ELISA procedure was followed as described in Example 6.

Two stable hybridomas were obtained following limited dilution cloning. One clone, 1C4F9, an IgM, was selected for further characterization. Ascitic fluid was raised in BALB/c mice, and 1C4F9 monoclonal antibody (mAb) was purified from ascitic fluid using an IgM-specific affinity column (PIERCE™, Rockford, Ill.) according to the manufacturer's protocol.

Studies of the specificity of the glucan-specific antibody were carried out using a series of linear oligosaccharides consisting of consecutive α1,6-linked glucose residues Glc→[α(1→6)Glc]$_{n=1-6}$ and selective purified *H. pylori* LPS. For inhibition ELISA, serial dilutions of linear α1,6-linked glucose-containing oligosaccharides from isomalto-series [Glcα1→(6Glcα1→)$_{n=1-6}$] (USBiologicals, Swampscott, Miss.) or *H. pylori* 26695, O:3 and PJ2 LPS inhibitors were prepared and mixed with previously prepared dilutions of purified 1C4F9 that gave an $OD_{450}=1$. Following the incubation (22° C., 15 min), this mixture was transferred to the original blocked microtiter plate with adsorbed LPS antigen, where it was incubated for another 2 h at 37° C. After this step, the indirect ELISA procedure was followed as described in Example 6. The percentage inhibition was calculated using the following formula:

% inhibition=100×[(OD with inhibitor−OD without inhibitor)/OD without inhibitor]

Inhibition versus log concentration curves were plotted for each inhibitor, and the concentrations required for the half maximal inhibitory concentration ($IC_{50}$) were determined from extrapolation curves.

The inhibitory properties optimized when using isomaltohexaose (n=5) and isomaltoheptaose (n=6) (Table 20). *H. pylori* PJ2 LPS previously shown to contain on average between six and eight residues in the glucan chain (Altman et al., 2003) was the most effective inhibitor (Table 20).

TABLE 20

Inhibition ELISA with a series of linear α1,6-linked glucose-containing oligosaccharides and LPS of *H. pylori* strains 26695, O:3 and PJ2.

| Inhibitor | $IC_{50}$[b] |
|---|---|
| Isomaltose | 0 |
| Glcα1→(6Glcα1→)$_{n=1}$ | |
| Isomaltotriose | 10,000 |
| Glcα1→(6Glcα1→)$_{n=2}$[a] | |
| Isomaltotetraose | 1,600 |
| Glcα1→(6Glcα1→)$_{n=3}$ | |
| Isomaltopentaose | |
| Glcα1→(6Glcα1→)$_{n=4}$ | 460 |
| Isomaltohexaose | 290 |
| Glcα1→(6Glcα1→)$_{n=5}$ | |
| Isomaltoheptaose | 210 |
| Glcα1→(6Glcα1→)$_{n=6}$ | |
| 26695 LPS (n=3-4) | 170 |
| O:3 LPS (n=5-6) | 52 |
| PJ2 LPS (n=6-8) | 0.29 |

[a]Number of α1,6-linked glucose residues.
[b]Concentration of the oligosaccharide or LPS (µg/mL) required for 50% inhibition.

Example 11

Accessibility Studies and Bactericidal Assays Using Anti-Glucan mAbs

Anti-glucan mAbs were readily accessible on the surface of live bacteria from representative *H. pylori* strains as demonstrated by indirect IF microscopy studies (Table 21). Both α1,6-glucan and CagA could be differentiated on the bacterial surface simultaneously.

To determine bactericidal activity of the monoclonal antibody, a ten-fold serial dilution of 1C4F9 mAb from de-complemented ascites (50 µL) was added to each well followed by bacterial suspension (25 µL) and pre-incubated for 15 min at 37° C. After this step, the procedure was followed as described in Example 7. The cell surface binding of 1C4F9 correlated with functional activity as determined by bactericidal assays against wild-type and mutant strains of *H. pylori* (Table 21).

TABLE 21

Characterization of 1C4F9 mAbs binding to α1,6-glucan of *H. pylori* strains by WCE, IF adherence and bactericidal assays.

| Strains | WCE ($OD_{450}$) | IF[a] | O-chain | $BC_{50}$ titre[b] |
|---|---|---|---|---|
| 26695 | 1.03 | ++++ | +[c] | 1:2 × 10$^6$ |
| 26695 HP0826::Kan | 1.347 | ++++ | −[d] | 1:2 × 10$^5$ |
| O:3 | 1.509 | ++++ | +[c] | 1:1 × 10$^6$ |
| O:3 HP0826::Kan | 1.372 | ++++ | −[d] | 1:4 × 10$^6$ |
| PJ1 | 1.573 | ++++ | −[c] | 1:2 × 10$^3$ |
| PJ2 | 1.659 | ++++ | −[e] | 1:6 × 10$^4$ |
| SS1 | − | − | +[c] | n.d.[d] |

[a]Symbols: ++++, strongly positive; −, negative.
[b]Bactericidal ($BC_{50}$) titres are represented as the reciprocal of the dilution of antiserum that reduced viable cell count by 50%.
[c]From Monteiro, 2001.
[d]From Logan et al., 2000.
[e]From Altman et al., 2003.
[d]Not determined.

While the preferred embodiments of the invention have been described above, it will be recognized and understood that various modifications may be made therein, and the appended claims are intended to cover all such modifications which may fall within the spirit and scope of the invention.

REFERENCES

All patents, patent applications and publications referred to herein and throughout the application are hereby incorporated by reference.

Altman E, Chandan V, Larocque S, Aubry A, Logan S M, Vinogradov E, Li J. Effect of the HP0159 ORF mutation on the lipopolysaccharide structure and colonizing ability of *Helicobacter pylori*. *FEMS Immunol Med Microbiol* 2008; 53: 204-213.

Altman E, Fernández H, Chandan V, Harrison B A, Wilson Schuster M, Otth Rademacher L, Toledo C. Analysis of *Helicobacter pylori* isolates from Chile: occurrence of a selective type 1 Lewis b antigen expression in lipopolysaccharide. *J Med Microbiol* 2008; 57: 585-591.

Altman E, Harrison B A, Hirama T, Chandan V, To R, MacKenzie R. Characterization of murine monoclonal antibodies against *Helicobacter pylori* lipopolysaccharide specific for Le$^x$ and Le$^y$ blood group antigens. *Biochem Cell Biol* 2005; 83: 589-596.

Altman E, Smirnova N, Li J, Aubry A, Logan S M. Occurrence of a nontypable *Helicobacter pylori* strain lacking Lewis blood group O antigens and DD-heptoglycan: evidence for the role of the core alpha1,6-glucan in colonization. *Glycobiology* 2003; 13: 777-783.

Anderson P W, Pichichero M E, Insel R A, Betts R, Eby R, Smith D H. Vaccines consisting of periodate-cleaved oligosaccharides from the capsule of *Haemophilus influenzae* type b coupled to a protein carrier: structural and temporal requirements for priming in the human infant. *J Immunol* 1986; 137: 1181-1186.

Angelakopoulos H, Hohmann E L. Pilot study of phoP/phoQ-deleted *Salmonella enterica* serovar Typhimurium expressing *Helicobacter pylori* urease in adult volunteers. *Infect Immun* 2000; 68: 2135-2141.

Appelmelk B J, Simmons-Smit L, Negrini R, Moran A P, Aspinall G O, Forte J G et al. Potential role of molecular mimicry between *Helicobacter pylori* lipopolysaccharide and host Lewis blood group antigens in autoimmunity. *Infect Immun* 1996; 64: 2031-2040.

Brisson J-R, Crawford E, Uhrin D, Khieu N H, Perry M B, Severn W B, Richards J C. The core oligosaccharide component from Mannheimia (Pasteurella) haemolytica serotype A1 lipopolysaccharide contains L-glycero-D-manno- and D-glycero-D-manno-heptoses: Analysis of the structure and conformation by high-resolution NMR spectroscopy. *Can J Chem* 2002; 80: 949-963.

Castillo-Rojas G, Mazari-Hiriart M & López-Vidal Y (2004). *Helicobacter pylori*: focus on CagA and VacA major virulence factors. *Salud pública de México* 46: 538-548.

Chandan V, Logan S M, Harrison B A, Vinogradov E, Aubry A, Stupak J, Li J, Altman, E. Characterization of a waaF mutant of *Helicobacter pylori* strains 26695 provides evidence that an extended lipopolysaccharide structure has a limited role in the invasion of gastric cancer cells. *Biochem Cell Biol* 2007; 85: 582-590.

Chu C, Liu B, Watson D, Szu S, Bryla D, Shiloach J, Schneerson R, Robbins J B. Preparation, characterization, and immunogenicity of conjugates composed of the O-specific polysaccharide of *Shigella dysenteriae* type 1 (Shiga's bacillus) bound to tetanus toxoid. *Infect Immun* 1991; 59: 4450-4458.

Ciucanu I, Kerek F. A simple and rapid method for the permethylation of carbohydrates. *Carbohydr Res* 2004; 131: 209-217.

Ciucanu I, Kerek, F. A simple and rapid method for the permethylation of carbohydrates. *Carbohydr Res* 2004, 131: 209-217.

Cox A D, Zou W, Gidney M A J, Lacelle S, Plested J S, Makepeace K, Wright J C, Coull P A, Moxon E R, Richards J C. Candidacy of LPS-based glycoconjugates to prevent invasive meningococcal disease: Developmental chemistry and investigation of immunological responses following immunization of mice and rabbits. *Vaccine* 2005; 23: 5045-5054.

Dubois M, Gilles K A, Hamilton J K, Rebers P A, Smith, F. Colorimetric method for determination of sugars and related substances. *Anal Chem* 1956; 28: 350-356.

Dunn B E, Cohen H, Blaser M J. *Helicobacter pylori*. *Clin Microbiol Rev* 1997; 10: 720-741.

Ellman G L. Tissue sulfhydryl groups. *Arch Biochem Biophys* 1959; 82: 70-77.

Fernández-Santana V, González-Lio R, Sarracent-Pérez J, Verez-Bencomo V. Conjugation of 5-azido-3-oxapentyl glycosides with thiolated proteins through the use of thiophilic derivatives. *Glycoconjugate J* 1998; 15: 549-553.

Gu X-X, Tsai C-M, Ueyama T, Barenkamp S J, Robbins J B, Lim D J. Synthesis, characterization, and immunological properties of detoxified lipooligosaccharide from nontypable *Haemophilus influenzae* conjugated to proteins. *Infect Immun* 1996; 64: 4047-4053.

Hiratsuka K, Logan S M, Conlan J W, Chandan V, Aubry A, Smirnova N, Ulrichsen H, Chan K H N, Griffith D W, Harrison B A, Li J, Altman E. Identification of a D-glycero-D-manno-heptosyltransferase gene from *Helicobacter pylori*. *J Bacteriol* 2005; 187: 5156-5165.

Holst O, Brade L, Kosma P, Brade, H. Structure, serological specificity, and synthesis of artificial glycoconjugates representing the genus-specific lipopolysaccharide epitope of *Chlamydia* spp. *J Bacteriol* 1991; 173:1862-1866.

Kabat E A. Chapter 11. Molecular Biology of Anti-α-(1→6) dextrans. Antibody responses to a Single-Site-Filling Antigenic Determinant. In: Carbohydrate Antigens (vol. 159). Garegg P J, Lindberg A A, eds. ACS Symposium Series, Washington: American Chemical Society, 1993; 146-58.

Kohler G, Milstein C. Continuous cultures of fused cells secreting antibody of predefined specificity. *Nature* 1975; 256: 495-497.

Logan S M, Altman E, Mykytczuk O, Brisson J-R, Chandan V, St Michael F, Masson A, Leclerc S, Hiratsuka K, Smirnova N, Li J, Wu Y, Wakarchuk W W. Novel biosynthetic functions of lipopolysaccharide rfaJ homologs from *Helicobacter pylori*. *Glycobiology* 2005; 15: 721-733.

Logan S M, Conlan J W, Monteiro M A, Wakarchuk W W, Altman E. Functional genomics of *Helicobacter pylori*: identification of a β-1,4 galactosyltransferase and generation of mutants with altered lipopolysaccharide. *Mol Microbiol* 2000; 35: 1156-1167.

Mieszala M, Kogan G, Jennings H J. Conjugation of meningococcal lipooligosaccharides through their lipid A terminus conserves their epitopes and results in conjugate vaccines having improved immunological properties. *Carbohydr Res* 2003; 338: 167-175.

Monteiro M A. *Helicobacter pylori*: a wolf in sheep's clothing: the glycotype families of *Helicobacter pylori* lipopolysaccharides expressing histo-blood groups: structure, biosynthesis, and role in pathogenesis. *Adv Carbohydr Chem Biochem* 2001; 57: 99-158.

Passwell J H, Ashkenazi S, Harlev E, Miron D, Ramon R, Farzam N, Lerner-Geva L, Levi Y, Chu C, Shiloach J, Robbins J B, Schneerson R, Israel *Shigella* Study Group. Safety and immunogenicity of *Shigella sonnei*-CRM9 and *Shigella flexneri* type 2α-rEPAsucc conjugate vaccines in one- to four-year old children. *Pediatr Infect Dis J* 2003; 22: 701-706.

Passwell J H, Harlev E, Ashkenazi S, Chu C, Miron D, Ramon R, Farzan N, Shiloach J, Bryla D A, Majadly F, Roberson R, Robbins J B, Schneerson R. Safety and immunogenicity of improved *Shigella* O-specific polysaccharide-protein conjugate vaccines in adults in Israel. *Infect Immun* 2000; 69: 1351-1357.

Pon R A, Lussier M, Yang Q-L, Jennings H J. N-Propionylated group B meningococcal polysaccharide mimics a unique bactericidal capsular epitope in group B *Neisseria meningitidis*. *J Exp Med* 1997; 185: 1929-1938.

Rossi G, Ruggiero P, Peppoloni S, Pancotto L, Fortuna D, Lauretti L, Volpini G, Mancianti S, Corazza M, Taccini E, Di Pisa F, Rappuoli R, Del Giudice G. Therapeutic vaccination against *Helicobacter pylori* in the beagle dog experimental model: safety, immunogenicity, and efficacy. *Infect Immun* 2004; 72: 3252-3259.

Roy, R., Katzenellenbogen, E., and Jennings, H. J. 1984. Improved procedures for the conjugation of oligosaccharides to protein by reductive amination. *Can J. Biochem. Cell Biol*. 62, 270-275.

Ruggiero P, Peppoloni S, Rappuoli R, Del Giudice G. The quest for a vaccine against *Helicobacter pylori*: how to move from mouse to man? *Microbes Infect* 2003; 5: 749-756.

Sawardeker J H, Sloneker J H, Jeannes A. Quantitative determination of monosaccharides as their alditol acetates by gas liquid chromatography. *Anal Chem* 1967; 39: 1602-1604.

Westphal, O Jann K. Bacterial polysaccharides. Extraction with phenol-water and further applications of the procedure. *Meth Carbohydr Chem* 1965; 5: 83-91.

Wirth H P, Yang M, Karita M, Blaser M J. Expression of the human cell surface glycoconjugates Lewis X and Lewis Y by *Helicobacter pylori* isolates is related to cagA status. *Infect Immun* 1996; 64: 4598-4605.

Yokota, S., Amano, K., Fujii, N., Yokochi, T. Comparison of serum antibody titers to *Helicobacter pylori* lipopolysaccharides, CagA, VacA and partially purified cellular extracts in a Japanese population. *FEMS Microbiol Lett* 2000; 185: 193-198.

Yu S, Gu X-X. Biological and immunological characteristics of lipooligosaccharide-based conjugate vaccines for serotype C *Moraxella catarrhalls*. *Infect Immun* 2007; 75: 2974-2980.

The invention claimed is:

1. A composition comprising an effective amount of a purified α1,6-glucan-containing *Helicobacter pylori* compound comprising the structure of Formula I:

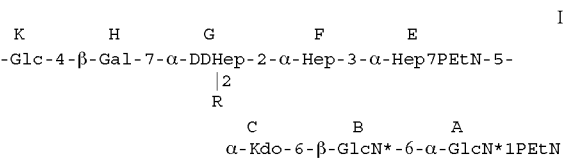

wherein the R is a α-DDHep-3-α-L-Fuc-3-β-GlcNAc trisaccharide substituted with an α1,6-glucan comprising from 4 to 12 α1,6-linked glucose residues linked to an α1,3-DD-heptan, wherein the last DD-Hep residue of the α1,3-DD-heptan is capped with β-GlcNAc residue and an effective amount of an adjuvant.

2. The compound of claim 1, wherein the heptan moiety comprises from 2 to 6 α1,3-linked heptose residues.

3. The compound of claim 1, wherein the R comprises

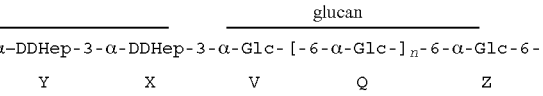

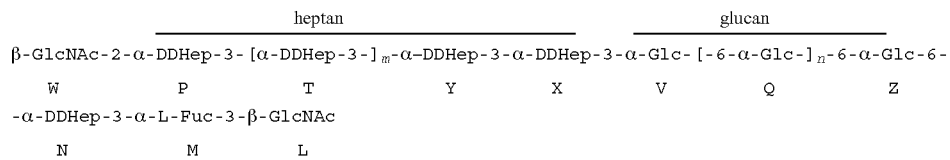

wherein the β-GlcNAc residue L is linked to O-2 of the Hep G, n=1 to 11, and m=0 to 4.

4. The compound of claim 3, wherein n=9.

5. The compound of claim 3, wherein m=2.

6. The compound of claim 1, wherein the structure of the Formula I further comprises a lipid A moiety covalently attached to the Kdo residue C.

7. The compound of claim 6, wherein the lipid A molecule is O-deacylated or is cleaved through hydrolysis of the ketosidic linkage of the Kdo residue.

8. The compound of claim 1, wherein the compound is isolated or purified from *H. pylori* strain HP0826::Kan.

9. A conjugate comprising a substantially linear α1,6-glucan-containing compound conjugated to an isolated protein carrier wherein the substantially linear α1,6-glucan-containing compound is the compound of claim 1, and wherein the compound is conjugated to the protein carrier, or the combination thereof via the Kdo residue.

10. The conjugate of claim 9, wherein the protein carrier is tetanus toxoid, bovine serum albumin, or CRM197.

11. A composition comprising:
an isolated α1,6-glucan-containing *Helicobacter pylori* compound comprising the structure of Formula I:

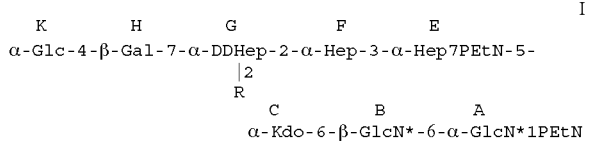

wherein the R is a α-DDHep-3-α-L-Fuc-3-β-GlcNAc trisaccharide substituted with an α1,6-glucan comprising from 4 to 12 α1,6-linked glucose residues linked to an α1,3-DD-heptan, wherein the last DD-Hep residue of the α1,3-DD-heptan is capped with β-GlcNAc residue; or a conjugate comprising an isolated α1,6-glucan-containing *Helicobacter pylori* compound comprising the structure of Formula I wherein the R is a α-DDHep-3-α-L-Fuc-3-β-GlcNAc trisaccharide substituted with an α1,6-glucan linked to an α1,3-DD-heptan, wherein the last DD-Hep residue of the α1,3-DD-heptan is capped with β-GlcNAc residue conjugated to an isolated protein carrier, wherein the compound is conjugated to the protein carrier, via the Kdo residue.

12. A method of inducing an immune response against *H. pylori* in an individual comprising administering to said individual an effective amount of the composition according to claim 11.

13. A composition comprising the conjugate of claim 9.

14. The conjugate of claim 9, wherein the compound is conjugated to the protein carrier via a linker or a spacer.

15. The conjugate of claim 11, wherein the compound is conjugated to the protein carrier via a linker or a spacer.

* * * * *